United States Patent [19]

Janssen et al.

[11] 4,017,631

[45] Apr. 12, 1977

[54] IMIDAZOLIUM SALTS

[75] Inventors: Paul Adriaan Jan Janssen, Vosselaar; Jan Heeres, Turnhout; Hubert Karel Frans Hermans, Gierle, all of Belgium

[73] Assignee: Janssen Pharmaceutica N.V., Beerse, Belgium

[22] Filed: Mar. 1, 1976

[21] Appl. No.: 662,998

Related U.S. Application Data

[60] Division of Ser. No. 525,142, Nov. 19, 1974, which is a continuation-in-part of Ser. No. 438,810, Jan. 31, 1974, abandoned.

[52] U.S. Cl. .......................... 424/273; 260/240 K; 260/307

[51] Int. Cl.$^2$ ...................... C07D 233/60

[58] Field of Search ................... 260/309, 240 K; 424/273

[56] References Cited

UNITED STATES PATENTS

| | | | |
|---|---|---|---|
| 3,493,581 | 2/1970 | Pommer et al. | 260/309 |
| 3,658,813 | 4/1972 | Godefroi et al. | 260/309 |
| 3,682,951 | 8/1972 | Kreider | 260/309 |
| 3,717,655 | 2/1973 | Godefroi et al. | 260/309 |

FOREIGN PATENTS OR APPLICATIONS

| | | | |
|---|---|---|---|
| 8,357M | 2/1971 | France | 260/309 |

OTHER PUBLICATIONS

Godefroi et al., Chem. Abst., 1970, vol. 72, No. 90,466v.

*Primary Examiner*—Natalie Trousof

[57] ABSTRACT

Novel quaternary imidazolium salts substituted on one nitrogen of the imidazolium cation with a

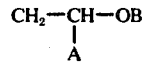

group in which each A is an aryl radical and B is an aliphatic, aryl-substituted aliphatic or aromatic radical, said salts being useful as antimicrobial agents.

3 Claims, No Drawings

IMIDAZOLIUM SALTS

CROSS-REFERENCE TO RELATED APPLICATIONS

This is a division of co-pending application Ser. No. 525,142, filed Nov. 19, 1974, which in turn is a continuation-in-part of our formerly copending application Ser. No. 438,310, filed Jan. 31, 1974, now abandoned.

BACKGROUND OF THE INVENTION

This invention is related to quaternary imidazolium salts which are useful as antimicrobial agents for the control of bacterial and fungal organisms. Quaternary imidazolium salts of the present invention differ from those of the prior art in numerous ways. Among other differences they differ in the complex ether function on one nitrogen and in the substituents on the other nitrogen of the imidazole ring.

The prior art on the quaternary imidazolium salts may be represented by the following references:

1. Shikoku Kasei Kogyo K. K. — Jap. Pat. Appln. 70.03. 800-RDerw. Jap. Pat. Rep. Vol. R, No. 8 - Pharm. p. 3.
2. Druzhinina, A. A. and Kochergin, P. M., Chem. Abstr., 68, 49509r.
3. Godefroi, E. F., J. Org. Chem., 33, 860 (1968).
4. Overberger, C. G. et al., J. Org. Chem., 1965, 3580.
5. Sarasin, J., Helv. Chim. Acta, 7, 720 (1924).
6. B.A.S.F., Fr. 1,468,184, Chem. Abstr., 67, 81482 (1967).

DESCRIPTION OF THE PREFERRED EMBODIMENTS

This invention relates to novel quaternary imidazolium salts, more particularly to salts represented by the formula

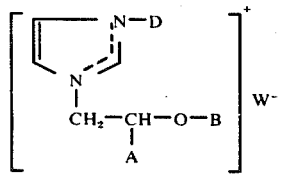

(I)

and hydrates thereof.

In this and succeeding formulas A may be an aromatic radical including aromatic heterocyclic radicals but preferably is selected from the group consisting of phenyl, mono-, di- and trihalophenyl, lower alkyphenyl, lower alkoxyphenyl, thienyl and halothienyl;

B may be a wholly aliphatic radical, an aryl-aliphatic radical or an aromatic radical, but is preferably selected from the group consisting of benzyl, mono-, di- and tri-halobenzyl, mono- and di-lower alkylbenzyl, lower alkoxybenzyl, cyanobenzyl, phenethyl, mono-, di- and tri-halophenethyl, lower alkoxyphenethyl, mono- and di-lower alkylphenethyl, cyanophenethyl, mono- and di-nitrophenyl, mono- and di-aminophenyl, lower alkyl, lower alkenyl and lower alkynyl; and D is a radical which at the point of attachment to the nitrogen of the imidazole ring is alkyl or substituted alkyl but in which the nature of the substituents may vary widely.

More specifically in the foregoing definitions of A and B, the expressions "lower alkyl" and "lower alkoxy" as employed in the definition of aryl-substituents, such as, for example, in the expressions lower alkylphenyl, lower alkylbenzyl, lower alkylphenethyl, lower alkoxyphenyl, lower alkoxybenzyl or lower alkoxyphenethyl, refer to a straight or branch chained hydrocarbon chain having from 1 to about 6 carbon atoms, such as, for example, methyl, ethyl, propyl, isopropyl, isobutyl, isoamyl, etc. and respectively the corresponding alkoxys, such as methoxy, ethoxy, isopropoxy, butoxy, etc.

"Lower alkyl" as employed in the definition of B as a whole has the meaning of a straight or branch chained hydrocarbon chain having from 1 to about 8 carbon atoms, such as, for example, methyl, butyl, sec. pentyl, n-heptyl, n-octyl, etc., and the expressions "lower alkenyl" and "lower alkynyl" refer to an unsaturated hydrocarbon radical having from 3 to about 5 carbon atoms wherein the unsaturation occurs in relation to the ether linkage preferably at the beta carbon atom, but which may also occur at the gamma or delta carbon atoms.

The expression "halo" in the foregoing definitions of A and B refers to a halogen atom of atomic weight less than 127, i.e., chloro, bromo, fluoro and iodo.

D may be more specifically defined as follows:
a. an alkyl radical containing from 1 to 12 carbon atoms;
b. a carbamoyl alkyl radical represented by the formula

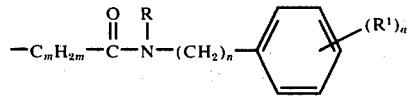

wherein R is selected from the group consisting of hydrogen and loweralkyl;
each $R^1$ is independently selected from the group consisting of hydrogen, lower alkyl, halo, nitro, trifluoromethyl, lower alkoxy and phenoxy;
$a$ and $m$ are integers of from 1 to 2 inclusive; and
$n$ is an integer of from 0 to 2 inclusive;
c. an aroyl-alkyl radical represented by the formula

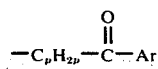

wherein Ar is selected from the group consisting of thienyl, halothienyl, phenyl, mono- and di-substituted phenyl and wherein each substituent in said substituted phenyl is selected independently from the group consisting of halo, lower alkyl, and lower alkoxy; and p is an integer of from 1 to 4 inclusive;
d. an aralkyl radical represented by the formula

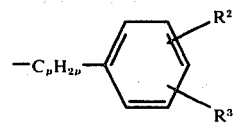

wherein $R^2$ is selected from the group consisting of hydrogen, halo, lower alkyl, lower alkoxy, nitro and sulfamoyl;

$R^3$ is selected from the group consisting of hydrogen, halo, lower alkyl, lower alkoxy and cyano;

and p is an integer of from 1 to 4 inclusive;

e. a diarylmethyl radical represented by the formula

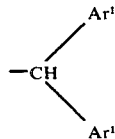

wherein each $Ar^1$ is selected independently from the group consisting of phenyl and halophenyl;

f. an arylaminoethyl radical represented by the formula

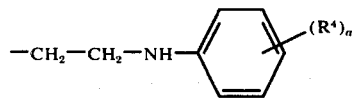

wherein each $R^4$ is independently selected from the group consisting of hydrogen, halo and lower alkyl; and a is an integer of from 1 to 2 inclusive;

g. an arylether-alkyl radical represented by the formula $-(CH_2)_q-Q-Ar^2$ wherein Q is selected from the group consisting of oxygen and sulfur;

$Ar^2$ is selected from the group consisting of phenyl, mono- and di-substituted phenyl and naphthyl, and wherein each substituent in said substituted phenyl is selected independently from the group consisting of halo, lower alkyl, lower alkoxy and allyl; and q is an integer of from 2 to 3 inclusive;

h. a dihydrobenzofuranylmethyl radical represented by the formula

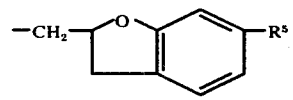

wherein $R^5$ is selected from the group consisting of hydrogen and halo;

i. an arylhydroxyethyl radical represented by the formula

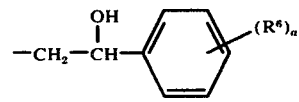

wherein $R^6$ is selected from the group consisting of hydrogen, halo and lower alkoxy, and a is an integer of from 1 to 2 inclusive;

j. an aralkenyl radical represented by the formula

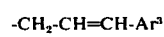
$-CH_2-CH=CH-Ar^3$ wherein $Ar^3$ is selected from the group consisting of phenyl, halophenyl, and di-halophenyl;

k. a phenoxy-2-oxopropyl radical represented by the formula

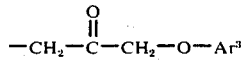

wherein $Ar^3$ is selected from the group consisting of phenyl, halophenyl and di-halophenyl;

and wherein by "lower alkyl" and "lower alkoxy" as employed in the foregoing definitions of D is meant a radical containing from 1 to 5 carbon atoms and by "halo" is meant chloro, bromo, fluoro and iodo.

The anion $W^-$ in the foregoing formula (I) may be any pharmaceutically acceptable anion but is preferably an ion arising from a reactive ester of the appropriate alcohol such as a halide ion, preferably chloride, bromide or iodide, or another ion arising from a reactive ester such as a methanesulfonate (mesylate) or p-toluenesulfonate (tosylate) ion. Other pharmaceutically acceptable anions falling within the scope of $W^-$ are, for example, anions arising from mineral acids, e.g. nitrate, sulfate and phosphate anions, and anions arising from organic acids, such as, for example, the anions of acetic, propionic, glycolic, lactic, pyruvic, malonic, succinic, maleic, fumaric, malic, tartaric, citric, benzoic, cinnamic, mandelic, ethanesulfonic, benzenesulfonic, cyclohexanesulfamic, salicylic, p-aminosalicylic and the like acids.

Anions arising from reactive esters in general are hereinafter represented by $Z^-$ and when the salts are chlorides, bromides or iodides the anion may be represented by $X^-$.

The novel compounds of formula (I) are generally crystalline solids and are frequently obtained as hydrates. The compounds have at least one, and frequently more than one, asymmetric center and therefore are obtained as racemates, in one or more isomeric forms, or may be resolved into one or more isomeric forms by methods known in the art. In addition, a number of the compounds have a double bond in their structure and may be obtained as a cis or trans isomer or a mixture of isomers which may be separated if desired. Isomers are intended to be within the scope of the invention.

The novel imidazolium salts of formula (I) are useful as antimicrobial aagents especially for the control of bacteria and fungi and may be employed as active ingredients in antiseptic and therapeutic compositions. Certain of the compounds have functional groups on the D substituent which are readily convertible to other functional groups; such compounds are therefore useful as intermediates for the preparation of other novel compounds.

The novel imidazolium salts of the present invention may be prepared by causing to react, an imidazole derivative of formula (II), wherein A and B have the previously indicated meaning with a reactive ester DZ (III) wherein D is as previously defined and Z is a reactive ester group, such as halo, methanesulfonyl (mesyl), p-toluenesulfonyl (tosyl), mesityl and the like, and if desired, exchanging the anion $Z^-$ in the thus-obtained compounds (I-a) for another therapeutically accceptable anion $W^-$ to obtain the desired salt of formula (I):

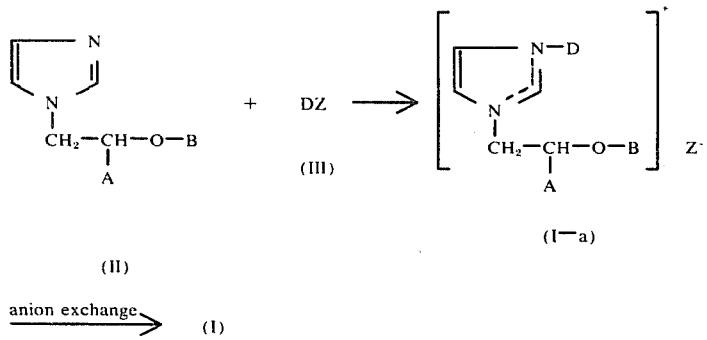

The reaction of (II) with (III) is carried out by stirring together the appropriate imidazole (II) and DZ (III) preferably in a suitable solvent. The exact proportion of the imidazole (II) and DZ is not critical, some of the desired imidazolium salt being obtained in any event. Good results have been obtained by employing substantially equimolar amounts.

Suitable solvents include nitriles such as acetonitrile, benzonitrile, and the like; halogenated lower hydrocarbons such as methylene chloride, tetrachloroethane and the like; lower alkanols such as methanol, ethanol, propanol, and the like; lower alkanones, such as acetone, 4-methyl-2-pentanone and the like; and other common solvents including dimethylformamide.

Somewhat elevated temperatures may be employed to enhance the rate of the reaction. It is convenient to carry out the reaction at the reflux temperature of the solvent. When D in DZ has an amino nitrogen within its structure, the reactant may be employed in the form of its acid addition salt. In such case, the inclusion of a suitable acid acceptor, preferably a metal base such as, for example, sodium carbonate or bicarbonate is appropriate.

Although many of the imidasolium salts require little or no purification, some of the salts are preferably subjected to one or more purification procedures. Suitable purification procedures include recrystallization, treatment with an adsorbent such as silic gel or charcoal, column-chromatography, washing, etc.

The compounds of formula (I) may alternatively be prepared by reacting an imidazole derivative of formula (IV) wherein D is as previously defined with a reactive ester of formula (V) wherein A, B and Z have the previously indicated meaning and, if desired, exchanging the anion of the thus-obtained compounds.

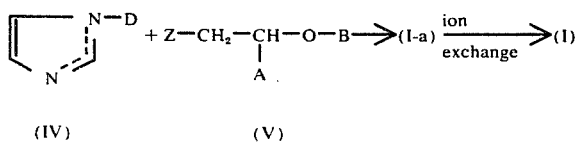

This reaction may be carried out in a manner analogous to that described for the preparation of (I) starting from the intermediates (II) and (III).

The conversion of an imidazolium salt into a different salt may be carried out according to art known methods.

One general method for accomplishing such conversion is to react an imidazolium salt with a base to form the corresponding imidazolium hydroxide and thereafter to react the imidazolium hydroxide with an appropriate acid to form a second imidazolium salt.

A convenient method consists in placing a solution of an imidazolium salt on an ion exchange resin column, in which the resin previously has been converted to the hydroxyl form, eluting the quaternary imidazolium hydroxide which is formed and adding a solution of the appropriate acid to the eluate, whereafter the desired salt is separated by conventional means. Suitable solvents for this operation are polar solvents, such as lower alkanols.

alternatively, an imidazolium salt may be converted to a second and desired salt by reacting the first salt with a large excess of an acid corresponding to the anion of the second salt. The reaction is preferably conducted in a polar solvent such as a lower alkanol, conveniently by refluxing and thereafter recovering by conventional means.

The imidazole derivatives of formula (II) are generally known. Such compounds and methods of preparing same are described in U.S. Pat. Nos. 3.658.813 and 3.717.655. They are generally prepared by O-alkylation of an appropriate imidazole-1-ethanol (VI).

for example, by contacting (VI), the hydroxyl of which has preliminarily been converted to an alkali metal salt by treatment with a strong base such as alkali metal amide, with an appropriate halide BX, wherein X is a halo group, preferably bromo or chloro. The imidazoles of formula (II) wherein B is an aminophenyl group are obtained by the reduction of the corresponding nitrophenyl compounds, for example, by catalytic hydrogenation such as contact with $H_2$ on Pd-C or with nascent hydrogen, e.g. Zn-HOAc, etc.

The D-Z compounds of formula (III) suitable for the practice of the present invention represent many classes of compounds and structural variations which correspond to the scope of the D substituent in the desired imidazolium salt.

The structural requirement of DZ is the presence of a halogen, methanesulfonate, p-toluenesulfonate, or other anion producing group of sufficient reactivity to quaternize the imidazole (II). It is desirable to have no more than one such reactive group. However, additonal unreactive halogen substituents may be present as a function on an aromatic ring or as a part of a radical such as trifluoromethyl.

Many of the DZ compounds which are halo compounds, i.e. compounds which may be represented by DX, are commercially available, or are described in the literature. Some of the compounds are novel and their preparation is subsequently described. All of the DZ compounds may be prepared employing methods known to those skilled in the art.

It is to be noted that some of the methods are preferred for the synthesis of chloro and bromo compounds and that the iodo compounds are preferably prepared from the corresponding chloro or bromo compound by the reaction of the latter with sodium iodide.

When the halo compound DX is a N-substituted heloalkylcarbonamide having the formula (VII)

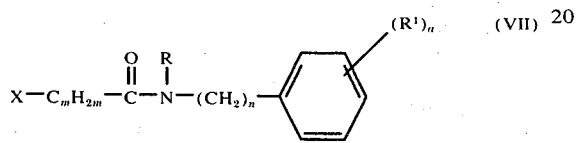

it may be prepared by reacting, preferably with cooling, an appropriate amine (VIII) or acid addition salt thereof with an appropriate haloacyl halide (IX) preferably in the presence of an acid acceptor such as for example, a tertiary amine or inorganic base, in a suitable solvent such as, for example, 1,2-dichloroethane; or alternatively, by simply heating the appropriate amine hydrogen halide with the haloacyl halide in a suitable organic solvent, such as dioxane; and thereafter recovering the N-substituted haloalkylcarbonamide from the reaction mixture by conventional procedures.

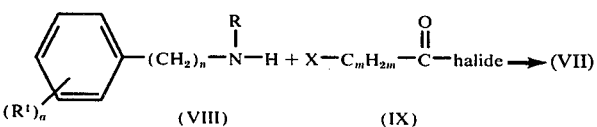

When DX is an aroyl alkyl halide represented by the formula (X)

the compounds are generally available or readily prepared by well known methods. When the halo compound (X) is an α-haloalkyl thienyl ketone or an α-haloacylophenone compound, it may be prepared by α-halogenation of an appropriate alkyl thienyl ketone or acylophenone, e. g. by intimately contacting the ketone with N-bromo-, N-chloro-, or N-iodo-succinimide in an inert solvent, e.g. carbon tetrachloride, preferably under reflux for several hours. When the halogen is at the terminal position of the chain, the compound may be prepared by Friedel-Crafts acylation, such as by reacting the ω-haloacyl halide under Friedel-Crafts conditions (e.g. for example excess aluminum chloride in carbon disulfide or nitrobenzene) with an appropriately substituted aromatic compound.

The halo compound (X) prepared by one of the foregoing procedures is recovered from the reaction mixture by conventional procedures.

When DX is an aralkyl halide represented by the formula (XI)

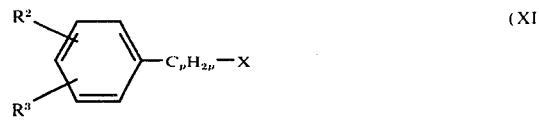

the compounds are known or may be prepared by conventional procedures such as side-chain halogenation of alkyl substituted aromatic hydrocarbons, replacement of the hydroxyl group in aromatic alcohols, replacement of one halogen for another in haloalkyl aromatic compounds, or Friedel-Crafts alkylation using a dihaloalkane.

The side-chain halogenation may be carried out in a manner similar to that employed in the preparation of α-haloacylophenone compounds, i.e., by heating with N-halosuccinimide in an inert solvent and recovering the product by conventional procedures.

The preparation of aralkyl halides by the replacement of a hydroxyl by a halogen may be carried out by well known methods such as by the dropwise addition of an inorganic halide such as thionyl chloride or phosphorus tribromide to the appropriate alkanol in an organic solvent, thereafter allowing the reaction to continue at ambient or moderately elevated temperatures for a period up to about 18 hours to obtain the desired aralkyl halides and recovering the product by conventional procedures.

Another preparative method which may be employed is the Friedel-Crafts alkylation using an α,ω-dihaloalkane. In such operation, the α,ω-dihaloalkane may be added with stirring and cooling under anhydrous conditions to a mixture of aluminum chloride and appropriately substituted benzene and carbon disulfide, followed by heating for several hours and the product recovered thereafter by conventional procedures.

When the aralkyl halide is an iodide, it is preferably prepared from the corresponding chloride or bromide by the replacement of that halogen with iodine. It is generally carried out by heating together the appropriate halogen compound and sodium iodide for from about one to ten hours and thereafter pouring the mixture into water to precipitate the aralkyl iodide and then recovering the product by conventional procedures.

The diarylmethyl halide starting materials represented by the formula (XII)

are known or easily prepared by methods described in the literature. They may be prepared, for example, by intimately contacting a diarylmethanol with an appropriate halogenating agent such as thionyl chloride or phosphorus tribromide in an inert solvent such as benzene; or with concentrated hydrochloric acid, for several hours preferably under reflux and thereafter recovering the diaryl halide. The reactant diarylmethanol it may be prepared through the following sequence of reactions:

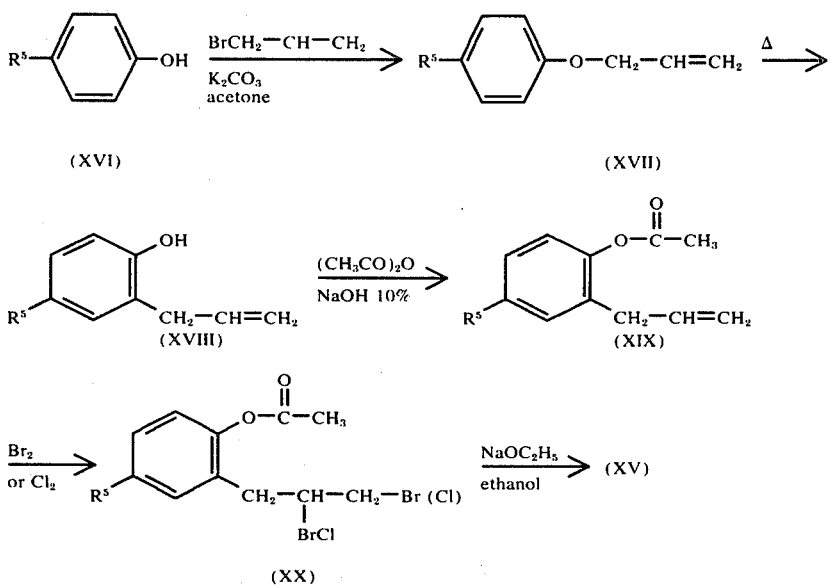

may be prepared by the reaction of an aromatic aldehyde and the Grignard reagent of an aromatic halide by conventional procedures.

The arylaminoethyl halide compounds represented by the formula (XIII)

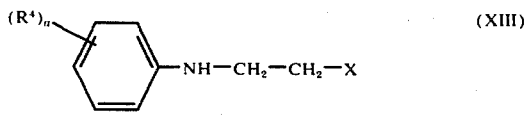

may be prepared by reacting an appropriate haloethanol with an appropriate arylamine by conventional methods such as, for example, refluxing in a solvent such as water to obtain an arylaminoethanol which after recovery by conventional methods is converted to an appropriate halide such as for example by contacting the arylaminoethanol with hydrogen halide, and thereafter recovering the arylaminoethyl halide thus obtained by conventional procedures.

When DX is an aryloxyalkyl halide or haloalkyl thioether represented by the formula

it may be prepared from the appropriate phenol or thiophenol and the appropriate dihaloalkane by heating substantially equimolar quantities of the reactants together in the presence of a base, and thereafter recovering the aryloxyalkyl halide or haloalkyl thioether thus obtained by conventional procedures.

When DX is a dihydrobenzofuranylmethyl bromide or chloride, of formula (XV)

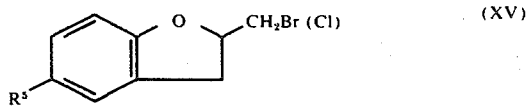

In the following operations, each of the intermediates are preferably recovered and purified by conventional procedures before proceeding with the next step:

In carrying out the first step of the reaction an appropriate phenol (XVI) is reacted with allyl halide in an appropriate solvent such as acetone in the presence of a base such as potassium carbonate.

The allylic rearrangement may be carried out by heating the allyloxybenzene product (XVII) at temperatures of from about 240° C to about 260° C to obtain the desired 2-allylphenol (XVIII).

The esterification step may be carried out by reacting an alkali metal (preferably sodium) salt of (XVIII) previously prepared by conventional methods, with an acylating agent such as acetic anhydride to obtain a allylacetoxybenzene (XIX).

The halogen addition step may be carried out by adding a halogenating agent (preferably bromine or chlorine) to a solution of (XIX) in an inert solvent such as carbon disulfide or a hydrocarbon whereby the desired (2,3-dihalopropyl)acetoxybenzene intermediate product (XX) is obtained.

Ring closure is subsequently performed with an appropriate cyclizing agent such as sodium ethoxide solution in ethanol whereby the desired 2-haloethyl-2,3-dihydro-5R-benzofuran (XV) is obtained.

When the DX compound is a α-halomethylbenzyl alcohol of formula (XXI)

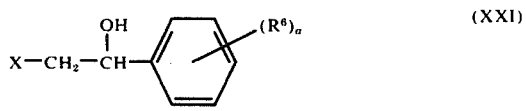

it may be prepared by the reduction of the corresponding α-haloacetophenone such as for example by intimately contacting with an appropriate reducing agent such as sodium borohydride and thereafter acidifying and recovering by conventional procedures.

When DX is a halocinnamyl halide represented by the formula (XXII)

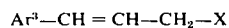 (XXII)

and Ar³ is halophenyl or dihalophenyl, it may be prepared by the allylic rearrangement of the appropriate halo-α-vinylbenzyl alcohol. In such operations the appropriate halo-α-vinylbenzyl alcohol and hydrohalic acid in an inert solvent, such as benzene and toluene, are shaken together whereupon an allylic rearrangement takes place with the formation of halocinnamyl halide which is then recovered by conventional procedures.

The aryloxy-2-oxopropyl halides of formula (XXIII)

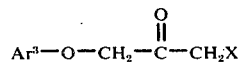

are readily prepared by oxidation of the corresponding alcohols with a strong oxidizing agent such as, for example, by intimately contacting with aqueous sodium dichromate in acid solution and thereafter recovering by conventional procedures.

The precursor alcohols are generally known and may be prepared by art known methods, such as by reacting a suitable metal phenolate with epichlorohydrin and cleavage of the resulting epoxide with an appropriate hydrogen halide.

When Z in DZ is methanesulfonate or p-toluenesulfonate or an anion from other reactive esters, DZ similarly may be obtained from the corresponding alcohol D-OH by esterification. The reaction may be carried out by adding p-toluenesulfonyl halide, methanesulfonyl halide, etc. to the D-OH compound in the presence of a base and recovering the ester by conventional procedures.

When DX is more readily available than D—OH, DX may be converted to D-OH by the reaction of the halo compound with freshly prepared moist silver oxide or by treating the halide with alkali acetate and saponifying the ester produced thereby. Thereafter, D-OH may be converted to the corresponding methanesulfonate or other reactive ester. The preparation of D-OH from DX may be carried out by adding DX to a slurry of moist silver oxide and stirring for from one to several hours, dissolving the resulting D-OH in a suitable solvent to separate it from the solid inorganic materials and recovering the product by conventional procedures.

The imidazolium salts of the present invention are useful as antimicrobial agents and may be employed as active ingredients in antibacterial and antifungal compositions for the control of organisms such as *Microsporum canis, Ctenomyces mentagrophytes, Trichophyton rubrum, Phialaphora verrucosa, Cryptococcus neoformans, Candida tropicalis, Candida albicans, Mucor species, Aspergillus fumigatus, Sporotrichum schenckii, Saprolegnia species, Salmonella pullorum gallinarum, Escherichia coli, Pseudomonas aeruginosa, Erysipelothrix insidiosa, Staphylococcus hemolyticus* and *Streptococcus pyogenes*.

Representative operations illustrating control of bacterial and fungal organisms by the imidazolium salts are hereinafter described:

Tests for the control of fungal organisms were performed using Sabouraud's liquid medium (1 g. of neopeptone Difco and 2 g. of glucose Difco per 100 ml. distilled water) in test tubes, each containing 4.5 ml. of liquid medium, autoclaved at 120° C for 15 minutes. The imidazolium salts were prepared for testing by dissolving in 50% ethanol to a concentration of 20 mg./ml. and thereafter diluting with sterile distilled water to obtain a concentration of 10 mg./ml. Successive decimal dilutions were then made with sterile distilled water to prepare a series of test solutions. In carrying out the test, 0.5 ml. of one of the test solutions is added to 4.5 ml. of Sabouraud's liquid medium to obtain a test medium. In this manner, from appropriate test solution, test media containing 100 µg, 10 µg, and 1 µg of imidazolium salt per milliliter of medium were obtained.

Control tubes were prepared by adding 0.5 ml. of sterile distilled water to 4.5 ml. of medium. Ethanol was also added to simulate the amount which would be present in the test media. Filamentous fungi were incubated at 25° C for two to three weeks. A square block of side 2 mm. was excised and inoculated into the liquid medium. A 3-day old culture on Sabouraud's liquid medium was used for yeasts. The inoculum was 0.05 ml. per tube. All cultures were incubated at 25° C for 14 days.

Table I illustrates the broad antifungal properties possessed by imidazolium salts of the present invention. The compounds listed in Table I showed complete inhibition of growth of eleven species of fungal organisms when the imidazolium salts were employed at a concentration of 100 µg/ml.

It is to be understood that the compounds in the following tables are not listed for the purpose of limiting the invention but to exemplify the useful properties of all the compounds within the scope of Formula I.

TABLE I

ANTIFUNGAL ACTIVITY

Imidazolium salts exhibiting 100% growth inhibition at 100 µg/ml against *Microsporum canis, Ctenomyces mentagrophytes, Trichophyton rubrum, Phialophora verrucosa, Cryptococcus neoformans, Candida tropicalis, Candida albicans, Mucor species, Aspergillus fumigatus, Sporotrichum schenckii, Saprolegnia sp.*

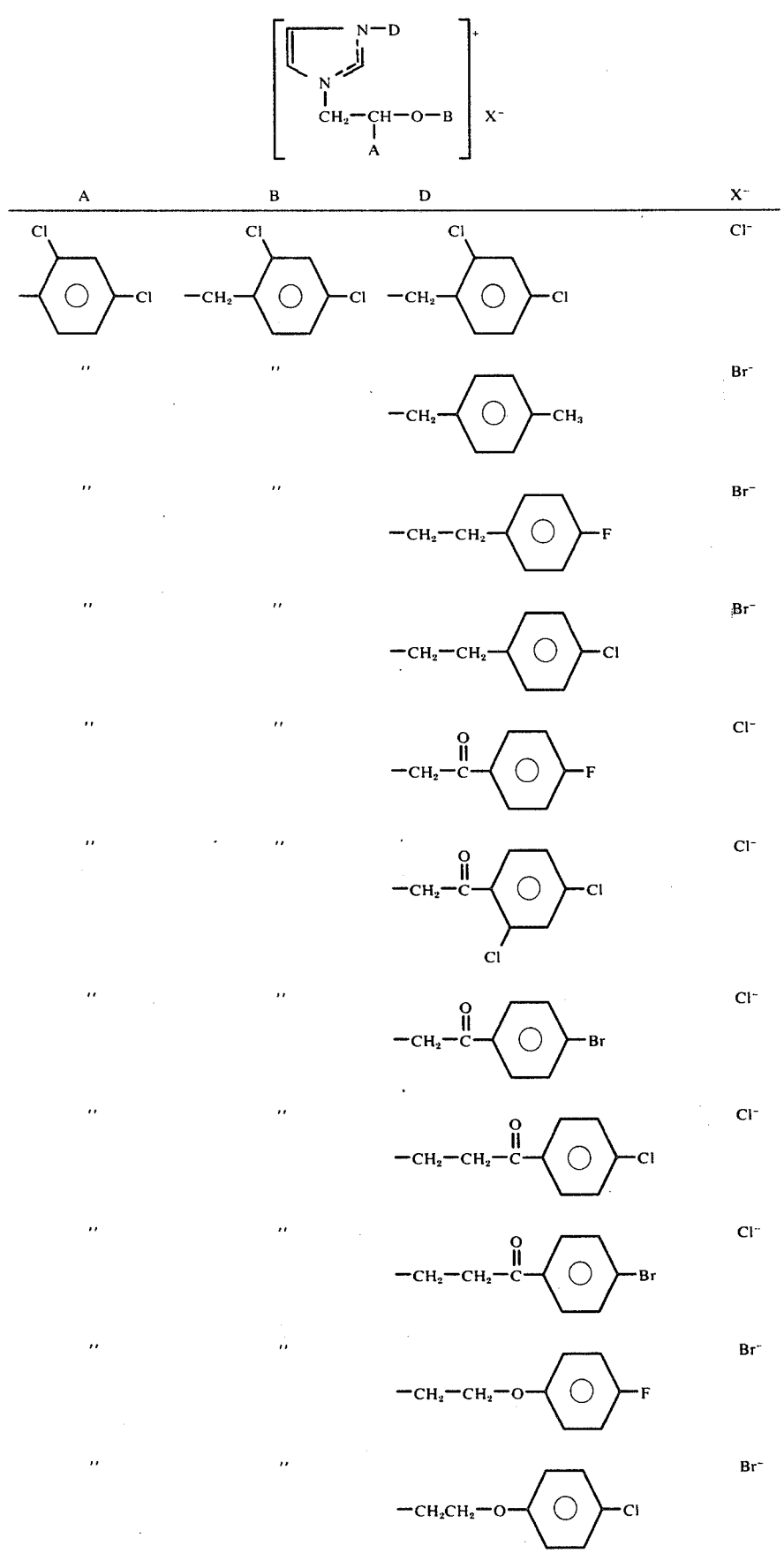

-continued
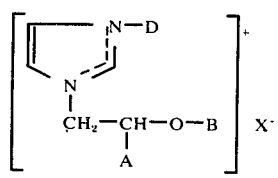
| A | B | D | X⁻ |
|---|---|---|---|
| " | " | | Br⁻ |
| " | " | —CH₂CH₂—O—(2,4-dichlorophenyl) | Br⁻ |
| " | " | —CH₂CH₂—O—(4-bromophenyl) | Br⁻ |
| " | " | —CH₂CH₂—O—(2-methylphenyl) | Br⁻ |
| " | " | —CH₂CH₂—O—(2,6-dimethylphenyl) | Br⁻ |
| " | " | —CH₂—CH₂—O—(naphthyl) | Br⁻ |
| " | " | —CH₂—CH₂—CH₂—O—(phenyl) | Br⁻ |
| " | " | —CH₂—CH₂—NH—(phenyl) | Br⁻ |
| " | " | —CH₂—C(=O)—NH—(2-chlorophenyl) | Cl⁻ |
| " | " | —CH₂—C(=O)—NH—(2-methylphenyl) | Cl⁻ |
| " | " | —CH₂—C(=O)—NH—(2,5-dimethylphenyl) | Cl⁻ |

-continued $$\left[\begin{array}{c} \diagup N-D \\ \diagdown N \\ | \\ CH_2-CH-O-B \\ | \\ A \end{array}\right]^+ X^-$$

| A | B | D | X⁻ |
|---|---|---|---|
| " | " | −CH₂−C(=O)−NH−(C₆H₄)−OCH₃ (meta-methoxyphenyl) | Cl⁻ |
| " | " | −CH₂−C(=O)−N(CH₃)−(2,6-dimethylphenyl) | Cl⁻ |
| " | " | −CH₂−C(=O)−N(C₂H₅)−(2,6-dimethylphenyl) | Cl⁻ |
| " | " | −CH(CH₃)−C(=O)−NH−C₆H₅ | Br⁻ |
| " | " | −CH₂−C(=O)−NH−CH₂−C₆H₅ | Cl⁻ |
| " | " | −CH(CH₃)−C(=O)−NH−CH₂−(2-chloro-6-methylphenyl) | Br⁻ |
| " | " | −CH₂CH₂−C(=O)−NH−(4-fluorophenyl) | Cl⁻ |
| " | " | −CH₂CH₂−C(=O)−NH−(4-chlorophenyl) | Cl⁻ |
| " | " | −CH₂CH₂−C(=O)−NH−(2-nitrophenyl) | Cl⁻ |
| " | " | −CH(CH₃)−C(=O)−(4-methylphenyl) | Br⁻ |
| " | " | −n−C₈H₁₇ | Br⁻ |

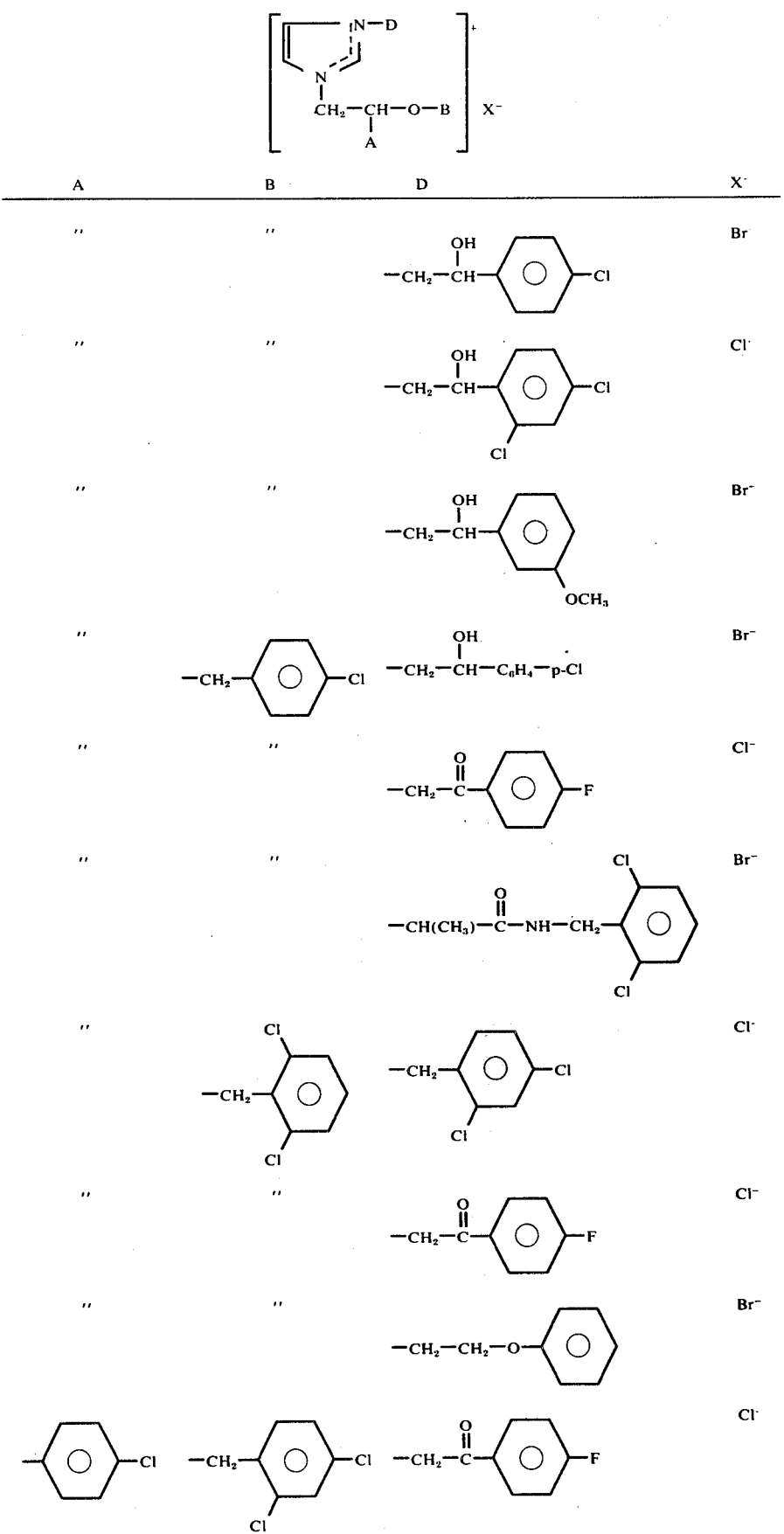

-continued

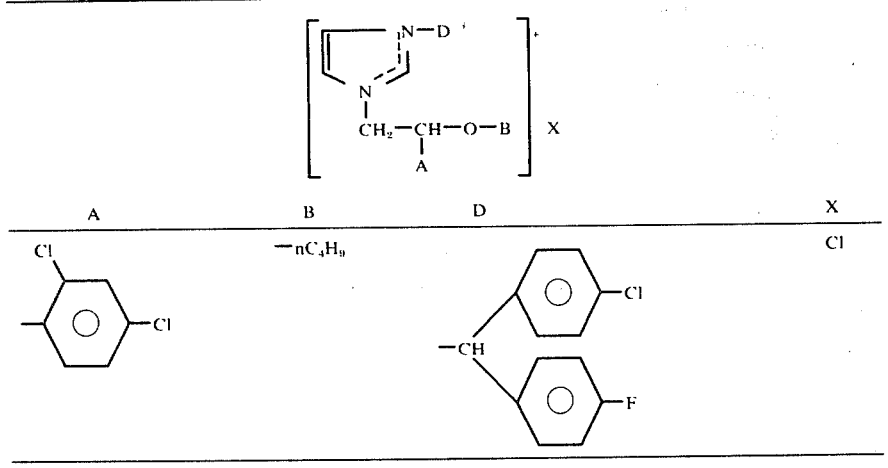

| A | B | D | X |
|---|---|---|---|
| 3,4-dichlorophenyl (Cl at 3, Cl at 4) | —nC₄H₉ | —CH(biphenyl: p-Cl, p-F) | Cl |

Table II illustrates the high effectiveness of many of the imidazolium salts of the present invention against a number of species of fungi. Thus, Table II shows with a number of imidazolium salts that 100% inhibition of growth of certain fungal organisms may be achieved with very minor concentrations of the imidazolium salt.

TABLE II

ANTIFUNGAL ACTIVITY

Imidazolium Salt

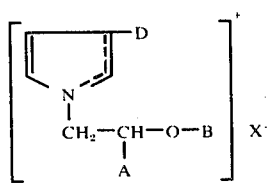

Concentrations in μg/ml for 100% Inhibition of Growth

ORGANISMS[1]

| A | B | D | X | M.c. | Ctm. | Tr.r | Cr.n. |
|---|---|---|---|---|---|---|---|
| 2,4—(Cl)₂—C₆H₃— | 2,4—(Cl)₂—C₆H₃—CH₂— | —CH₂—C₆H₃—3,4(CH₃)₂ | Cl | 10 | 1 | 1 | 10 |
| " | " | —CH₂—CO—C₆H₄—pF | Cl | 1 | 1 | 1 | 10 |
| " | " | —CH₂—CO—C₆H₄—pCl | Br | 1 | 1 | 1 | 1 |
| " | " | —CH₂—CO—C₆H₃—2,4(Cl)₂ | Cl | 10 | 1 | 1 | 1 |
| " | " | —CH₂—CO—C₆H₄—pBr | Cl | 10 | 1 | 1 | 1 |
| " | " | —CH₂—CO—C₆H₄—mOCH₃ | Br | 10 | 1 | 1 | 10 |
| " | " | —(CH₂)₂—CO—C₆H₄—pCl | Cl | 1 | 1 | 1 | 1 |
| " | " | —(CH₂)₂—CO—C₆H₄—pBr | Cl | 10 | 1 | 1 | 1 |
| " | " | —(CH₂)₂—O—C₆H₅ | Br | 10 | 10 | 1 | 10 |
| " | " | —(CH₂)₂—O—C₆H₄—pCH₃ | Br | 10 | 10 | 1 | 10 |
| " | " | —(CH₂)₂O—C₆H₃—2,6—(CH₃)₂ | Br | 10 | 1 | 10 | 1 |
| " | " | —(CH₂)₂OC₁₀H₇ | Br | 10 | 10 | 10 | 1 |
| " | " | —(CH₂)₂—NH—C₆H₄—pCl | Br | 10 | 10 | 10 | 1 |
| " | " | —CH₂—CO—NH—C₆H₄—o—CH₃ | Cl | 10 | 1 | 1 | 1 |
| " | " | —CH₂—CO—C₆H₄—p—(OCH₃) | Br | 10 | 10 | 1 | 10 |
| " | " | —(CH₂)₃O—C₁₀H₇ | Cl | 10 | 10 | 10 | 100 |
| " | " | —CH₂—CO—NH—C₆H₄—o—Cl | Cl | 10 | 10 | 1 | 10 |
| " | " | —CH₂—CO—NH—C₆H₃—2,4(Cl)₂ | Cl | 10 | 10 | 10 | 1 |
| " | " | —CH₂—CO—NH—C₆H₄—m—(OCH₃) | Cl | 10 | 10 | 1 | 10 |
| " | " | —CH₂—CO—NH—C₆H₄—o—OPh | Cl | 1 | 10 | 1 | 100 | ns

TABLE II-continued
ANTIFUNGAL ACTIVITY

Imidazolium Salt

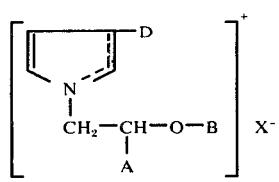

Concentrations in μg/ml for 100% Inhibition of Growth

ORGANISMS[1]

| A | B | D | X⁻ | M.c. | Ctm. | Tr.r | Cr.n. |
|---|---|---|---|---|---|---|---|
| " | " | —CH₂—CO—N(CH₃)—C₆H₃—2,6-(CH₃)₂ | Cl⁻ | 10 | 10 | 1 | 10 |
| " | " | —CH(CH₃)—CO—NH—C₆H₄—oCl | Br⁻ | 10 | 10 | 1 | 10 |
| " | " | —CH₂CO—NH—CH₂—C₆H₄—oCl | Cl⁻ | 1 | 10 | 1 | 10 |
| " | " | —CH(CH₃)—CO—NH—CH₂—C₆H₃(o-Cl)(o-CH₃) | Br⁻ | 1 | 1 | 1 | 10 |
| " | " | —(CH₂)₂—CO—NH—C₆H₄—oNO₂ | Cl⁻ | 10 | 1 | 1 | 10 |
| " | " | —CH₂—CH—CH—C₆H₅ | Cl⁻ | 10 | 10 | 1 | 100 |
| " | " | —CH₂—CH=CH—C₆H₃—2,4(Cl)₂ | Cl⁻ | 10 | 1 | 10 | 10 |
| " | " | —CH(C₆H₄-Cl)(C₆H₄-F) | Cl⁻ | 10 | 10 | 1 | 100 |
| " | " | —CH₂—CO—(2-thienyl) | Br⁻ | 10 | 1 | 1 | 10 |
| " | " | —CH₂—CO—(5-Cl-2-thienyl) | Br⁻ | 1 | 1 | 1 | 10 |
| " | " | n.C₈H₁₇ | Br⁻ | 10 | 10 | 1 | 100 |
| " | " | —CH₂—CH(OH)—C₆H₄—pCl | Br⁻ | 10 | 1 | 1 | 1 |
| " | " | —CH₂—CHOH—C₆H₃—2,4—(Cl)₂ | Cl⁻ | 1 | 1 | 1 | 10 |
| " | " | —CH₂—CHOH—C₆H₄—pCl | Br⁻ | 1 | 1 | 1 | 100 |
| —CH₂—C₆H₄—Cl | " | —CH₂—CO—C₆H₄—pF | Cl | 1 | 1 | 1 | 10 |
| —CH₂—C₆H₃(Cl)₂ | " | —CH₂—CHOH—C₆H₄—pCl | Br⁻ | 10 | 10 | 1 | 10 |
| " | " | —CH₂—CO—C₆H₄—pF | Cl⁻ | 10 | 10 | 1 | 10 |
| p—Cl—C₆H₄— | —CH₂—C₆H₃—2,4—(Cl)₂ | —CH₂—CO—C₆H₄—pF | Cl⁻ | 10 | 10 | 10 | 10 |
| " | —CH₂C₆H₄—pCl | —CH₂—CO—C₆H₄—pF | Cl⁻ | 10 | 10 | 10 | 10 |

TABLE II-continued
ANTIFUNGAL ACTIVITY

Imidazolium Salt

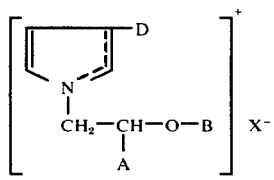

Concentrations in μg/ml for 100% Inhibition of Growth

ORGANISMS[1]

| A | B | D | X⁻ | M.c. | Ctm. | Tr.r | Cr.n. |
|---|---|---|---|---|---|---|---|
| " | " | —CH₂—CO—NH—C₆H₄—pF | Cl⁻ | —* | 1 | 10 | 100 |
| 2,4(Cl)₂—C₆H₃ | —CH₂CH=CH₂ | —CH₂—CO—C₆H₄—pF | Cl⁻ | 10 | 10 | 10 | 100 |
| " | —nC₄H₉ | —CH₂—CO—NH—C₆H₄—pF | Cl⁻ | 10 | 10 | 10 | 100 |
| " | " | —CH(C₆H₄—pCl)(C₆H₄—pCl) | Cl⁻ | 10 | 10 | 10 | 100 |
| " | —CH₂—C₆H₄—p—Cl | —CH₂—CO—NH—C₆H₄—o—CH₃ | Cl⁻ | 10 | 1 | 1 | 10 |

[1]M.c. = Microsporum canis; Ct.m. = Ctenomyces mentagrophytes; Tr.r = Trichophyton rubrum; Cr.n. = Cryptococcus neoformans
*Growth observed at 100 μg/ml.

Preferred compounds, particularly for their outstanding antifungal activity are imidazolium salts in which D is phenethyl or substituted phenethyl or in which D bears a carbonyl, carbamoyl, ether or alcohol function.

The compounds of the present invention also showed good antibacterial properties when representative operations were carried out on gram positive and gram negative organisms. The tests on bacteria were performed on cultures on phenol red dextrose broth medium (Difco). By using decimal dilution techniques described for the tests for antifungal activity, test media containing 100 μg, 10 μg and 1 μg of imidazolium salt per milliliter of medium were obtained. The inoculum consisted of a platinum loop (5 mm diameter) from a 24 hour broth culture. Forty-eight hours after incubation, subcultures were made from each culture for the determination of antibacterial activity of the imidazolium salts. After seven days of incubation, observations were made to determine the presence or absence of bacterial growth.

The tests indicated that many of the compounds showed broad activity and further that a number of the compounds showed very high activity against gram positive organisms. Table III shows results with representative compounds which demonstrate both broad activity and high activity toward representative gram positive organisms. Again, it is to be understood that the antibacterial properties listed in Table III are merely representative of the useful properties possessed by all the compounds within the scope of Formula I.

TABLE III
Antibacterial Activity

Imidazolium Salt

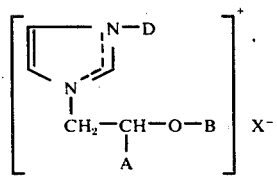

Concentration in μg for 100% Growth Inhibition

Organisms[1]

| A | B | D | X⁻ | Sp. G. | E. coli | Ps. aer. | E. ins | Staph. | Strep. |
|---|---|---|---|---|---|---|---|---|---|
| 2,4—(Cl)₂—C₆H₃— | 2,4—(Cl)₂—C₆H₃—CH₂— | —CH₂—C₆H₄—p—F | I⁻ | 10 | 100 | 100 | 10 | 1 | 1 |
| " | " | —CH₂C₆H₄—p—CH₃ | Br⁻ | 100 | 10 | 100 | 10 | 1 | 1 |
| " | " | —CH₂C₆H₃—3,4—(CH₃)₂ | Cl⁻ | 10 | 10 | 100 | 1 | 1 | 1 |
| " | " | —(CH₂)₂—C₆H₅ | Br⁻ | 10 | 10 | 100 | 1 | 1 | 1 |
| " | " | —(CH₂)₂C₆H₄—p—F | Br⁻ | 10 | 100 | 100 | 10 | 1 | 1 |
| " | " | —(CH₂)₂C₆H₄—p—OCH₃ | Cl⁻ | 10 | 100 | 100 | 1 | 1 | 1 |
| " | " | —CH₂—CO—C₆H₄—p—F | Cl⁻ | 10 | 10 | 100 | 1 | 1 | 1 |
| " | " | —(CH₂)₂—O—C₆H₅ | Br⁻ | 10 | 10 | 100 | 1 | 1 | 1 |

TABLE III-continued

Antibacterial Activity

Imidazolium Salt

Concentration in μg for 100% Growth Inhibition

Organisms[1]

| A | B | D | X⁻ | Sp. G. | E. coli | Ps. aer. | E. ins | Staph. | Strep. |
|---|---|---|---|---|---|---|---|---|---|
| " | " | —(CH₂)₂—O—C₆H₄—p—CH₃ | Br | 10 | 10 | 100 | 1 | 1 | 1 |
| " | " | —(CH₂)₂—NH—C₆H₅ | Br | 10 | 10 | 100 | 1 | 1 | 1 |
| " | " | —(CH₂)₂—NH—C₆H₃—<br>—2,6-(Cl)₂ | Br | 10 | 10 | 100 | 1 | 1 | 1 |
| " | " | —CH₂CONHC₆H₄—p—F | Cl | 10 | 10 | 100 | 1 | 1 | 1 |
| " | " | —CH₂CO—NH—C₆H₄—p-(Cl) | Cl | 100 | 10 | 100 | 1 | 10 | 1 |
| " | " | —CH₂CO—NH—C₆H₃—2,4-(Cl)₂ | Cl | 10 | 10 | 100 | 1 | 1 | 1 |
| " | " | —CH₂CO—NH—C₆H₄—o—CH₃ | Cl | 10 | 10 | 100 | 1 | 1 | 1 |
| " | " | —CH₂CO—NH—C₆H₄—o—OCH₃ | Cl | 10 | 10 | 100 | 1 | 1 | 1 |
| " | " | —CH₂CO—NH—C₆H₄—p—OCH₃ | Cl | 10 | 10 | 100 | 1 | 1 | 1 |
| " | " | —CH(CH₃)—CO—NH—C₆H₄—<br>—m—Cl | Br | 100 | 100 | 100 | 1 | 1 | 1 |
| " | " | —CH₂—CO—NH—CH₂—<br>—C₆H₄—p-CH₃ | Cl | 10 | 10 | 100 | 10 | 10 | 10 |
| " | " | —(CH₂)₂—CO—NH—<br>—C₆H₄—o-Cl | Cl | 10 | 10 | 100 | 1 | 1 | 1 |
| " | " | —(CH₂)₂CO—NH—<br>—C₆H₃—2,4(CH₃,Cl) | Cl | 10 | 100 | 100 | 1 | 1 | 1 |
| " | " | —CH(C₆H₄—p-Cl)(C₆H₄—p-F) | Cl | 100 | 100 | 100 | 1 | 1 | 1 |
| " | " | —CH(C₆H₄—p—F)(C₆H₅) | Cl | 10 | 10 | 100 | 1 | 1 | 1 |
| " | " | —CH₂CHOH—C₆H₄—p-Cl | Br | 10 | 10 | 100 | 1 | 1 | 1 |
| " | " | —CH₂—CHOH—C₆H₃—2,4(Cl)₂ | Cl | 10 | 10 | 100 | 1 | 1 | 1 |
| " | —CH₂C₆H₄—p-Cl | —CH₂—CHOH—C₆H₄—p—Cl | Br | 10 | 10 | 100 | 1 | 1 | 1 |
| " | " | —CH₂—CO—C₆H₄—p—F | Cl | 10 | 100 | 100 | 1 | 1 | 1 |
| " | —CH₂C₆H₃—2,6(Cl)₂ | —CH₂—C₆H₃—2,4(Cl)₂ | Cl | 10 | 10 | 100 | 1 | 1 | 1 |
| " | " | —CH₂—CO—NH—C₆H₄—p—F | Cl | 10 | 10 | 100 | 1 | 1 | 1 |
| " | " | —CH₂—CO—NH—C₆H₄—o—CH₃ | Cl | 10 | 100 | 100 | 10 | 10 | 1 |
| —C₆H₄—p—Cl | —CH₂—C₆H₃—2,4(Cl)₂ | —CH₂—CO—NH—C₆H₄—p—F | Cl | 10 | 10 | 100 | 1 | 10 | 1 |
| " | " | —CH₂—CO—NH—C₆H₄—o—CH₃ | Cl | 10 | 100 | 100 | 1 | 100 | 1 |
| " | —CH₂C₆H₄—p—Cl | —CH₂—CO—NH—C₆H₄—p—F | Cl | 10 | 100 | 100 | 10 | 10 | 1 |
| —C₆H₄—p—Cl | —CH₂—C₆H₄—p—Cl | —CH₂—CO—NH—C₆H₄—o—CH₃ | Cl | 100 | 100 | 100 | 10 | 10 | 10 |
| —C₆H₅ | " | —CH₂—C₆H₅ | Br | 100 | 100 | —* | 100 | 10 | 10 |
| —C₆H₄—o—Cl | —n—C₄H₉ | —CH₂—CO—NH—C₆H₄—p—F | Cl | 100 | 100 | 100 | 10 | 100 | 10 |

[1] Sp. G. = Salmonella pullerum gallinarum; E. coli = Escherichia coli; Ps. aer. = Pseudomonas aeruginosa; E. ins. = Erysipelothrix insidiosa; Staph. = Staphylococcus hemolyticus; Strep. = Streptococcus pyogenes.

In view of the aforementioned anti-fungal and antibacterial activities, this invention provides valuable compositions comprising the imidazolium salts (I) as the active ingredient in a solvent or a solid, semi-solid or liquid diluent or carrier, and, in addition, it provides an effective method of combatting fungus or bacterial growth by use of an effective anti-fungal or anti-bacterial amount of such imidazolium salts (I). The imidazolium salts can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin are also suitable carrier substances.

The imidazolium salt is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, pulverous preparations can also be made readily wettable with water, so that suspensions are obtained.

Inert solvents used for the production of liquid preparations should preferably not be readily inflammable and so far as possible non-toxic to warm-blooded animals or plants in the relevant surroundings. Solvents suitable for this purpose are high-boiling oils, for example, of vegetable origin, and lower-boiling solvents, such as, for example, isopropanol, dimethylsulfoxide, hydrogenated napthalenes and alkylated napthalenes. It is of course, also possible to use mixtures of solvents. Solutions can be prepared in the usual way, if necessary, with assistance of solution promoters. Other liquid forms which can be used consist of emulsions or suspensions of the active compound in water or suitable inert solvents, or also concentrates for preparing such emulsions, which can be direction adjusted to the required concentration. For this purpose, the imidazolium salt is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the imidazolium salt can be incorporated, if necessary, with the aid of solution promoters and/or emulsifiers. Vaseline and other cream bases are examples of semi-solid carrier substances.

Furthermore, it is possible for the imidazolium salt to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g. in closed chambers and storage rooms, and for application to vegetation for eradicating or for preventing infection by fungi or bacteria.

The imidazolium salts and compositions thereof can be applied by conventional methods. For example, a fungus or bacterial growth or a material to be treated or to be protected against attack by fungus or bacterium can be treated with the imidazolium salts and the compositions thereof by dusting, sprinkling, spraying, brushing, dipping, smearing, impregnating or other suitable means.

When the imidazolium salts are employed in combination with suitable carriers, e.g., in solution, suspension, dust, powder, ointment, emulsion and the like forms, a high activity over a very high range of dilution is observed. For example, concentrations of the active ingredient ranging from 0.1-10 percent by weight, based on the weight of composition employed, have been found effective in combatting fungi or bacteria. Of course, higher concentrations may also be employed as warranted by the particular situation.

The following examples are intended to illustrate but not to limit the scope of the invention. Unless otherwise stated all parts are by weight.

A. PREPARATIONS OF INTERMEDIATES:

EXAMPLE I

To a stirred mixture of 5.7 parts of lithium aluminum hydride in 20 parts of ether is added dropwise a solution of 15 parts of 2-cyano-3-chlorotoluene in 140 parts of ether at reflux temperature. After the addition is complete, stirring at reflux temperature is continued for one hour. The reaction mixture is cooled in an ice-bath and decomposed with 25 parts of water and with a 20% solution of potassium-sodium tartrate (450 parts). The aqueous phase is separated and extracted with ether. The combined ether layers are washed with water, dried, filtered and evaporated. The oily residue is distilled in vacuo, yielding 12 parts of 2-chloro-6-methylbenzylamine; bp. 113°–118° C at 18 mm. pressure.

A mixture of 35 parts of 2-chloro-6-methylbenzylamine and 30 parts of triethyl amine in 400 parts of ethylene chloride is stirred and cooled to −35°C. While keeping the temperature between −35° and −20° C., there is added dripwise a solution of 50 parts of 2-bromopropionyl bromide in 160 parts of ethylene chloride. Upon completion, the whole is stirred for one hour at room temperature. The reaction mixture is washed with diluted hydrochloric acid and once with water. The organic phase is dried over magnesium sulfate, filtered and evaporated. The solid residue is crystallized from a mixture of 400 parts of ethanol and 150 parts of water, yielding 40 parts of N-(2-bromopropionyl)-2-chloro-6-methylbenzylamine; mp. 168°–169° C.

EXAMPLE II

To a stirred and cooled solution of 322 parts of α,α,α-trifluoro-m-toluidine and 800 parts of anhydrous benzene is added dropwise a solution of 126 parts of 3-chloropropionyl chloride in 400 parts of anhydrous benzene at a temperature of about 10° C. Upon completion, the cooling-bath is removed and stirring is continued for one hour at room temperature. Then there are added 1000 parts of hydrochloric acid solution 5%. The precipitated starting material is filtered off. From the filtrate, the organic layer is separated, washed with water, dried, filtered and evaporated. The solid residue is crystallized from a mixture of diisopropyl ether and petroleum ether, yielding 180 parts of 3-chloro-α,α,α-trifluoro-m-propionotoluidide; mp. 68° C.

EXAMPLE III

To a stirred and cooled mixture of 33 parts of N-benzyl-N-tert.-butylamine in 60 parts of sodium hydroxide solution 20% and 160 parts of 1,2-dichloroethane are added dropwise 34 parts of 2-chloroacetyl chloride at a temperature between −5° and −10° C. Upon completion, stirring is continued at the same temperature for one hour. The reaction mixture is allowed to reach room temperature and the organic layer is separated, washed with water, dried and evaporated, yielding 43 parts of N-benzyl-N-tert.-butyl-2-chloroacetamide as a residue.

EXAMPLE IV

A mixture of 336.3 parts of 4-fluorophenol, 417.5 parts of allyl bromide, 420 parts of potassium carbonate and 480 parts of acetone is stirred and refluxed for 8 hours. After cooling to room temperature, 2250 parts of water are added. The aqueous layer is separated and extracted twice with ether. The combined extracts are washed successively twice with sodium hydroxide solution 10% and twice with sodium chloride solution, dried over potassium carbonate, filtered and evaporated. The oily residue is distilled in vacuo, yielding 381.8 parts of 4-allyloxy-fluorobenzene; bp. 93° C at 23 mm. pressure; $n_D^{20}$: 1.4950; $d_{20}^{20}$: 1.070.

381.8 parts of oily 4-allyloxy-fluorobenzene are heated in an oil-bath for 8 hours at a temperature of about 245°–250° C. After cooling, the reaction mixture is poured onto 1200 parts of hexane. The mixture is extracted three times with sodium hydroxide solution 20% (total volume of sodium hydroxide: 2000 parts). The aqueous layer is washed with petroleum ether, acidified with 1300 parts of concentrated hydrochloric acid solution and extracted with ether. The extract is dried over calcium chloride, filtered and evaporated. The oily residue is distilled in vacuo, yielding 313.6 parts of 2-allyl-4-fluorophenol; bp 143° C at 48 mm. pressure; $n_D^{20}$: 1.5225; $d_{20}^{20}$: 1.1130.

602 parts of sodium hydroxide solution 10% are cooled to 0° C. While keeping the temperature at about 5° C., there is added successively 150.5 parts of 2-allyl-4-fluorophenol and 656 parts of crushed ice. Upon completion, the cooling-bath is removed and there is added dropwise 112 parts of acetic anhydride at a temperature of about 15° C. The whole is stirred vigorously for 3 hours at room temperature, whereafter it is extracted with tetrachloromethane. The extract is washed twice with 250 parts of a sodium carbonate solution 10%, dried over potassium carbonate, filtered and evaporated. The oily residue is distilled in vacuo, yielding 156.3 parts of 3-allyl-4-acetoxy-fluorobenzene; bp. 125° C at 10 mm. pressure.

A mixture of 156.3 parts of oily 3-allyl-4-acetoxy-fluorobenzene in 650 parts of carbon disulfide is cooled in an ice-salt bath to 0° C.. While keeping the temperature between 0° and −6° C. there are added, during a 1.8 hour period; 134.4 parts of bromine (exothermic reaction). Upon completion, the whole is stirred for 2 hours at room temperature. The organic layer is washed with water, dried over magnesium sulfate, filtered and evaporated. The oily residue is distilled in vacuo, to yield 231.7 parts of 3-(2,3-dibromopropyl)-4-acetoxy-fluorobenzene; bp. 165°–167° C at 1.5 mm. pressure.

A sodium ethoxide solution, prepared in the conventional manner starting from 15.2 parts of sodium in 100 parts of ethanol, is added dropwise to a mixture of 231 parts of 3-(2,3-dibromopropyl)-4-acetoxy-fluorobenzene in 800 parts of ethanol (exothermic reaction: temperature rises to 50° C.). Upon completion, stirring is continued for 2 hours at reflux temperature. The reaction mixture is cooled to room temperature, filtered from some insoluble matter and the filtrate is evaporated. The residue is divided between water and ether. The aqueous layer is separated and extracted once more with ether. The combined ethereal phases are dried over calcium chloride, filtered and evaporated. The oily residue is distilled in vacuo, yielding 102 parts of 2-bromomethyl-2,3-dihydro-5-fluorobenzofuran; bp. 100°–105° C. at 1.5 mm. pressure.

EXAMPLE V

To a stirred and refluxing mixture of 162 parts of 2-allyl-4-fluorophenol, 363 parts of 1,3-dibromopropane in 700 parts of water is added dropwise a solution of 56 parts of sodium hydroxide in 175 parts of water. Upon completion, the whole is stirred and refluxed for 8 hours. After cooling, the aqueous layer is separated and extracted with chloroform. The extract is dried over magnesium sulfate, filtered and evaporated. The oily residue is distilled twice, yielding 142 parts of 3-allyl-4-(3-bromopropoxy)fluorobenzene; bp. 160°–170° C. at 14 mm. pressure.

EXAMPLE VI

To a stirred and gently refluxing mixture of 256 parts of butyl (5-nitro-o-tolyl)ether, 1 part of benzoyl peroxide and 4800 parts of anhydrous carbon tetrachloride is added, over a one-day period, a mixture of 213.6 parts of N-bromosuccinimide and 1 part of benzoyl peroxide. Upon completion, stirring at gentle reflux is continued overnight. The reaction mixture is cooled and water is added. The organic layer is separated, washed with water, dried, filtered and evaporated. The oily residue is crystallized on standing overnight in 2-propanol, yielding 189.7 parts of (α-bromo-5-nitro-o-tolyl) butyl ether; mp. 64° C.

EXAMPLE VII

A. To a stirred suspension of 44.2 parts of 1-chloro-3-(p-chlorophenoxy)-2-propanol in 75 parts of water are added 32.3 parts of sodium dichromate dihydrate. Then there is added dropwise, during a 5-hour period, a solution of 45 parts of sulfuric acid in 25 parts of water at a temperature <30° C. Upon completion, stirring is continued for 48 hours. The reaction mixture is poured onto water and the product is extracted twice with diisopropyl ether. The combined extracts are washed three times with water, dried, filtered and evaporated. The residue solidifies on scratching in ether. The solid product is crystallized from diisopropyl ether, yielding 25.2 parts of 1-chloro-3-(p-chlorophenoxy)-2-propanone.

B. By repeating the procedure of Example VII-A and using therein an equivalent amount of respectively 1-chloro-3-(p-bromophenoxy)-2-propanol or 1-chloro-3-(2,4-dichlorophenoxy)-2-propanol in place of the 1-chloro-3-(p-chlorophenoxy)-2-propanol the following compounds are respectively obtained: 1-(p-bromophenoxy)-3-chloro-2-propanone; and 1-chloro-3-(2,4-dichlorophenoxy)-2-propanone.

EXAMPLE VIII

To a stirred and cooled mixture of 18.6 parts of 3-(m-chlorophenoxy)propanol in 50 parts of pyridine are added dropwise 17.5 parts of mesyl chloride at a temperature below 10° C.. Upon completion, stirring is continued for 3 hours at room temperature. The reaction mixture is poured onto water and the product is extracted twice with benzene. The combined extracts are washed four times with a 20% hydrochloric acid solution, dried, filtered and evaporated, yielding 23 parts of 3-(m-chlorophenoxy)propanol, methanesulfonate ester as a residue.

EXAMPLE IX

A mixture of 12 parts of sodium iodide, 40 parts of toluene and 30 parts of sulfolan is stirred for 2 hours at reflux temperature with water-separator. Then there are added 11 parts of p-(2-chloroethyl)benzenesulfonamide and stirring and refluxing is continued for 3 hours. The reaction mixture is cooled and poured onto 300 parts of water. The precipitated product is filtered off, washed successively with water, with a sodium thiosulfate solution and again with water. After crystallization of the crude product from ethanol, 12.5 parts of p-(2-iodoethyl)benzenesulfonamide are obtained; m.p. 226.6° C.

B. PREPARATION OF THE FINAL PRODUCTS OF FORMULA I:

EXAMPLE X 4.2 Parts of 1-[2,4-dichloro-β-(2,4-dichlorobenzyloxy)-phenethyl]imidazole, 3.7 parts of p-chlorobenzyl iodide and 56 parts of methylene chloride are mixed together and stirred at reflux temperature for five hours to obtain a 1-(p-chlorobenzyl)-3-[2,4-dichloro-β-(2,4-dichlorobenzyloxy)phenethyl]imidazolium iodide product which remains in the reaction mixture. The reaction mixture is warmed to evaporate off the solvent and to recover the product as residue. The crude product is purified by washing with 2-propanol and crystallizing from a mixture of 4-methyl-2-pentanone and diisopropyl ether, to yield 1-(p-chlorobenzyl)-3-[2,4-dichloro-β-(2,4-dichlorobenzyloxy)phenethyl]imidazolium iodide; m.p. 145°–148° C.

EXAMPLE XI 4.2 parts of 1-[2,4-dichloro-β-(2,4-dichlorobenzyloxy)phenethyl]imidazole, 2.6 parts of 2-(p-tolyloxy)ethyl bromide and 40 parts of methylene chloride are mixed together and stirred at reflux temperature for 48 hours. The solvent is evaporated off and crude 1-[2,4-dichloro-β-(2,4-dichlorobenzyloxy)phenethyl]-3-[2-(p-tolyloxy)ethyl]imidazolium bromide recovered as residue.

The crude product is purified by a series of purification steps. First, the product is washed by stirring in a mixture of 4-methyl-2-pentanone and ether and thereafter filtered. The washed product is then subjected to chromatographic purification by dissolving in chloroform, placing the chloroform solution on a silicugel column of 50 centimeters, eluating with 5% methanol in chloroform, and vaporizing off the solvent from the eluate. The residue from the eluate is washed with a mixture of 4-methyl-2-pentanone and ether and filtered to obtain a purified product, 1-[2,4-dichloro-β-(2,4-dichlorobenzyloxy)phenethyl]-3-[2-(p-tolyloxy)ethyl]imidazolium bromide, which after drying overnight at 70° C melts at 126.5°–128° C.

EXAMPLE XII

In a manner similar to that described in Example XI, the following compounds are prepared by carrying out the reaction in methylene chloride solvent and employing chromatographic adsorption techniques in the purification and isolation of the resulting products.

1-[2,4-Dichloro-β-(2,4-dichlorobenzyloxy)phenethyl]-3-(p-fluorobenzyl)-imidazolium iodide; mp. 151°–153° C., by the reaction of 1-[2,4-dichloro-β-(2,4-dichlorobenzyloxy)phenethyl]-imidazole and p-fluorobenzyl iodide.

1-[2,4-Dichloro-β-(2,4-dichlorobenzyloxy)phenethyl]-3-(o-nitrobenzyl)imidazolium bromide; mp. 138.5°–141° C., by the reaction of 1-[2,4-dichloro-β-(2,4-dichlorobenzyloxy)phenethyl]-imidazole and o-nitrobenzyl bromide.

1-[2,4-Dichloro-β-(2,4-dichlorobenzyloxy)phenethyl]-3-(m-methylbenzyl)imidazolium bromide; mp. 99°–101° C., by the reaction of 1-[2,4-dichloro-β-(2,4-dichlorobenzyloxy)phenethyl]-imidazole and m-methylbenzyl bromide.

1-[2,4-Dichloro-β-(2,4-dichlorobenzyloxy)phenethyl]-3-(p-methylbenzyl)imidazolium bromide; mp. 152.2° C., by the reaction of 1-[2,4-dichloro-β-(2,4-dichlorobenzyloxy)phenethyl]-imidazole and p-methylbenzyl bromide.

1-[2,4-Dichloro-β-(2,4-dichlorobenzyloxy)phenethyl]-3-(2-ethoxy-5-nitrobenzyl)imidazolium iodide; mp. 193.6° C., by the reaction of 2-(iodomethyl)-4-nitrophenetole and 1-[2,4-dichloro-β-(2,4-dichlorobenzyloxy)phenethyl]imidazole.

EXAMPLE XIII

In a manner similar to that previously described, 4.2 parts of 1-[2,4-dichloro-β-(2,4-dichlorobenzyloxy)-phenethyl]imidazole, 1.7 parts of 2-chloro-4'-fluoroacetophenone and 40 parts of methylene chloride are mixed together and stirred at reflux temperature for 15 hours. Thereafter, the solvent is evaporated under reduced pressure and the residue triturated in 4-methyl-2-pentanone. The solid is recovered by filtration and crystallized from acetonitrile to obtain a purified 1-[2,4-dichloroβ-(2,4-dichlorobenzyloxy)phenethyl]-3-(p-fluorobenzoylmethyl)imidazolium chloride product, m.p. 181° C.

EXAMPLE XIV

In a manner similar to that described in Example XIII, 1-(2,4-dichlorobenzoylmethyl)-3-[2,4-dichloro-β-(2,4-dichlorobenzyloxy)phenethyl]imidazolium chloride is prepared by the reaction of 1-[2,4-dichloro-β-(2,4-dichlorobenzyloxy)phenethyl]imidazole and 2,2',4'-trichloroacetophenone. The product after crystallization from a mixture of 2-propanol and diisopropyl ether has a melting point of 186° C.

EXAMPLE XV

In a manner similar to that described in Examples XIII and XIV, 1-(p-bromobenzoylmethyl)-3-[2,4-dichloro-β-(2,4-dichlorobenzyloxy)phenethyl]imidazolium chloride is prepared by the reaction of 1-[2,4-dichloro-β-(2,4-dichlorobenzyloxy)phenethyl]imidazole and 4'-bromo-2-chloroacetophenone. The product after successive treatment steps of stirring with 4-methyl-2-pentanone, stirring a chloroform solution thereof with silica gel and triturating with 4-methyl-2-pentanone has a melting point of 198.2° C.

EXAMPLE XVI 15 parts of 1-[2,4-dichloro-β-(2,4-dichlorobenzyloxy)phenethyl]imidazole and 60 parts of 2,4-dichlorobenzyl chloride are mixed together in 120 parts of acetone as solvent and the resulting mixture is stirred at reflux temperature for 40 hours. At the end of this period, the mixture is warmed to evaporate off most of the solvent and the residue is poured onto diisopropyl ether, whereupon the 1-(2,4-dichlorobenzyl)-3-[2,4-dichloro-β-(2,4-dichlorobenzyloxy)phenethyl]imidazolium chloride product separates as an oil. The ether is decanted off and the oily residue is washed with warm xylene and thereafter triturated in 2-propanol whereupon the oily product solidified. The solid product is filtered off, washed with 2-propanol and dried to obtain a purified product, 1-(2,4-dichlorobenzyl)-3-[2,4-dichloro-β-(2,4-dichlorobenzyloxy)phenethyl]imidazolium chloride, m.p. 178.9° C.

EXAMPLE XVII 4.2 parts of 1-[2,4-dichloro-β-(2,4-dichlorobenzyloxy)-phenethyl]imidazole and 2.7 parts of α-bromo-5-nitrotoluonitrile are mixed together in 24 parts of methanol as solvent and the resulting mixture is stirred at reflux temperature overnight. At the end of this period, the solvent is evaporated off to obtain a crude 1-(2-cyano-4-nitrobenzyl)-3-[2,4-dichloro-β-(2,4-dichlorobenzyloxy)phenethyl]imidazolium bromide product as a residue. The residue is purified by triturating in acetone, and crystallizing from a mixture of methanol and diisopropyl ether to yield pure 1-(2-cyano-4-nitrobenzyl)-3-[2,4-dichloro-β-(2,4-dichlorobenzyloxy)phenethyl]imidazolium bromide; m.p. 171°–173° C.

EXAMPLE XVIII

In a manner similar to that described in Example XVII, crude 1-(p-chlorobenzoylmethyl)-3-[2,4-dichloro-β-(2,4-dichlorobenzyloxy)phenethyl]imidazolium bromide is prepared by the reaction of 1-[2,4-dichloro-β-(2,4-dichlorobenzyloxy)phenethyl]imidazole and 2-bromo-4′-chloroacetophenone after a 6 hour reflux in methanol. After recovery and purification by triturating in a mixture of 4-methyl-2-pentanone - diisopropyl ether and crystallizing from acetonitrile - diisopropyl ether, the product has a melting point of 165°–169° C.

EXAMPLE XIX 6.2 parts of 1-[p-chloro-β-(2,4-dichlorobenzyloxy)-phenethyl]imidazole and 3.4 parts of 2-chloro-p-fluoroacetophenone in 80 parts of acetonitrile are stirred together at reflux temperature for 24 hours. At the end of this period, the reaction mixture is allowed to cool to room temperature whereupon the desired 1-[p-chloro-β-(2,4-dichlorobenzyloxy)phenethyl]-3-(p-fluorophenacyl)imidazolium chloride product separates as a crystalline solid. The latter is recovered by filtration and dried, yielding 7 parts of 1-[p-chloro-β-(2,4-dichlorobenzyloxy)phenethyl]-3-(p-fluorophenacyl)imidazolium chloride; mp. 180.1° C.

EXAMPLE XX

In operations carried out at the reflux temperature of acetonitrile, in a manner similar to that described in Example XIX, the following compounds are prepared:

1-[p-chloro-β-(2,4-dichlorobenzyloxy)phenethyl]-3-[N-(p-fluorophenyl)carbamoyl-methyl]imidazolium chloride, mp. 203.4° C., by the reaction of 7.6 parts of 1-[p-chloro-β-(2,4-dichlorobenzyloxy)phenethyl]imidazole and 4.2 parts of 2-chloro-p-fluoroacetanilide after a 6 hour reflux.

1-(p-chloro-β-hydroxyphenethyl)-3-[2,4-dichloro-β-(2,6-dichlorobenzyloxy)phenethyl]imidazolium bromide; mp. 214° C., by the reaction overnight (about 15 hours) of 8.3 parts of 1-[2,4-dichloro-β-(2,6-dichlorobenzyloxy)phenethyl]imidazole and 4.7 parts of α-(bromomethyl)-p-chlorobenzyl alcohol.

1-[2,4-dichloro-β-(2,6-dichlorobenzyloxy)phenethyl]-3-[N-(p-fluorophenyl)carbamoylmethyl]imidazolium chloride, mp. 166°–192.5° C., by the reaction overnight of 8.3 parts of 1-[2,4-dichloro-β-(2,6-dichlorobenzyloxy)phenethyl]imidazole and 3.75 parts of 2-chloro-4′-fluoroacetanilide.

1-[2,4-dichloro-β-(2,6-dichlorobenzyloxy)phenethyl]-3-(N-o-tolylcarbamoylmethyl)imidazolium chloride; mp. 168.6° C., by the reaction overnight of 8.3 parts of 1-[2,4-dichloro-β-(2,6-dichlorobenzyloxy)-phenethyl]imidazole and 4.04 parts of 2-chloroaceto-o-toluidide.

Similarly, the reaction of 8.3 parts of 1-[2,4-dichloro-β-(2,4-dichlorobenzyloxy)phenethyl]imidazole and 4.9 parts of 2-bromo-4′-fluoropropionanilide after an overnight reflux yielded 8 parts of a 1-[2,4-dichloro-β-(2,4-dichlorobenzyloxy)phenethyl]-3- 1-[N-(p-fluorophenyl)carbamoyl]ethyl imidazolium bromide product; mp. 165.1°–168.2° C. From the mother liquor, a second fraction is obtained by vaporizing off the solvent which after recrystallization from 4-methyl-2-pentanone yielded 2 parts of product of m.p. 183.1° C.

EXAMPLE XXI

A mixture of 6.6 parts of 1-[β-(p-chlorobenzyloxy)-phenethyl]imidazole, 4.2 parts of methyl iodide and 24 parts of acetonitrile is stirred and refluxed for 4 hours. Upon the addition of 80 parts of ether, the quaternary salt is precipitated. It is filtered off and crystallized from a mixture of 24 parts of acetone and 24 parts of diisopropyl ether, yielding 5 parts of 1-[β-(p-chlorobenzyloxy)phenethyl]-3-methylimidazolium iodide; mp. 112° C.

EXAMPLE XXII

A. A mixture of 4.2 parts of 1-[2,4-dichloro-β-(2,4-dichlorobenzyloxy)phenethyl]imidazole, 2.7 parts of 2,4-dichlorocinnamylchloride and 40 parts of acetonitrile is stirred and refluxed overnight. Upon the addition of diisopropyl ether, the product crystallizes. It is filtered off and dried, yielding 5.8 parts of 1-(2,4-dichlorocinnamyl)-3-[2,4-dichloro-β-(2,4-dichlorobenzyloxy)phenethyl]imidazolium chloride; mp. 142.2° C.

B. In reactions carried out in a manner similar to that described in Example XXII-A, the following compounds are prepared:

1-[2,4-dichloro-β-(2,4-dichlorobenzyloxy)phenethyl]-3-[N-(2,5-xylyl)carbamoylmethyl]imidazolium chloride; mp. 178° C., from 1-[2,4-dichloro-β-(2,4- dichlorobenzyloxy)phenethyl]imidazole and 2-chloroaceto-2',5'-xylidide after an overnight reflux.

1-decyl-3-[2,4-dichloro-β-(2,4-dichlorobenzyloxy)-phenethyl]imidazolium bromide; mp. 90°–94° C., by the reaction of 1-[2,4-dichloro-β-(2,4-dichlorobenzyloxy)phenethyl]imidazole and n-decyl bromide after an overnight reflux.

1-[2,4-dichloro-β-(2,4-dichlorobenzyloxy)phenethyl]-3-n-octylimidazolium bromide; mp. 141.5°–143° C., from 1-[2,4-dichloro-β-(2,4-dichlorobenzyloxy)-phenethyl]imidazole and n-octyl bromide after an overnight reflux.

EXAMPLE XXIII

A mixture of 8 parts of 1-[2,4-dichloro-β-(2,4-dichlorobenzyloxy)phenethyl]imidazole, 5.6 parts of 2-bromo-N-(p-methylbenzyl)propionamide and 80 parts of acetonitrile is stirred and refluxed for 20 hours. The reaction mixture is evaporated and the residue is crystallized from a mixture of 4-methyl-2-pentanone and diisopropyl ether, yielding 9 parts of 1-[2,4-dichloro-β-(2,4-dichlorobenzyloxy)phenethyl]-3- 1-[N-(p-methylbenzyl)carbamoyl]ethyl -imidazolium bromide; mp. 136.2° C.

EXAMPLE XXIV

In reactions carried out in a manner similar to that described in Example XXIII, and the product isolated in such similar manner but using one of the alternative purification procedures of washing, triturating or recrystallizing as hereinafter indicated, the following compounds are prepared:

1-[3-(2-allyl-4-fluorophenoxy)propyl]-3-[2,4-dichloro-β-(2,4-dichlorobenzyloxy)phenethyl-]imidazolium bromide by the reaction of 1-[2,4-dichloro-β-(2,4-dichlorobenzyloxy)phenethyl-]imidazole and 3-allyl-4-(3-bromopropoxy)fluorobenzene. The product after purification by washing with 4-methyl-2-pentanone and diisopropyl ether melted from 134° to 138° C.

1-[2,4-dichloro-β-(2,4-dichlorobenzyloxy)phenethyl]-3-[N-(m-methoxyphenyl)carbamoylmethyl-]imidazolium chloride hydrate by the reaction of 1-[2,4-dichloro-β-(2,4-dichlorobenzyloxy)phenethyl-]imidazole and 2-chloroaceto-m-anisidide. The product after recrystallizing from 4-methyl-2-pentanone melted from 109° to 116.4° C. 116.5°

1-[2,4-dichloro-β-(2,4-dichlorobenzyloxy)phenethyl]-3-[N-(2,6-dichlorophenyl)carbamoylmethyl-]imidazolium chloride by the reaction of 1-[2,4-dichloro-β-(2,4-dichlorobenzyloxy)phenethyl-]imidazole and 2,2',6'-trichloroacetanilide. The product after washing with 4-methyl-2-pentanone and ether has a melting point of 140.9° C.

1-(p-chloro-β-hydroxyphenethyl)-3-[2,4-dichloro-β-(2,4-dichlorobenzyloxy)phenethyl]imidazolium bromide, from 1-[2,4-dichloro-β-(2,4-dichlorobenzyloxy)-phenethyl]imidazole and α-(bromomethyl)-p-chlorobenzyl alcohol. The product after trituration in acetone melted 171.5° to 186° C.

1-[N-(p-chlorophenyl)carbamoylmethyl]-3-[2,4-dichloro-β-(2,4-dichlorobenzyloxy)phenethyl-]imidazolium chloride hydrate, by the reaction of 1-[2,4-dichloro-β-(2,4-dichlorobenzyloxy)phenethyl-]imidazole and 2,4'-dichloroacetanilide. The product after trituration in 4-methyl-2-pentanone has a melting range of 92°–107° C. 1-[2,4-dichloro-β-(2,4-dichlorobenzyloxy)phenethyl]-3-[N-(o-methoxyphenyl)carbamoylmethyl]imidazolium chloride hydrate, by the reaction of 1-[2,4-dichloro-β-(2,4-dichlorobenzyloxy)phenethyl]imidazole and 2-chloro-2'-methoxyacetanilide. The product after washing with 4-methyl-2-pentanone has a m.p. of 137°–147° C.

1-[bis(p-chlorophenyl)methyl]-3-[2,4-dichloro-β-(2,4-dichlorobenzyloxy)phenethyl]imidazolium chloride by the reaction of 1-[2,4-dichloro-β-(2,4-dichlorobenzyloxy)phenethyl]imidazole and chloro-bis(p-chlorophenyl)methane. The product after recrystallization from 4-methyl-2-pentanone has a m.p. of 161.7° C.

EXAMPLE XXV

In a similar manner 4.2 parts of 1-[2,4-dichloro-β-(2,4-dichlorobenzyloxy)phenethyl]imidazole, 2.5 parts of 2-chloroaceto-N-ethyl-2',6'-xylidide and 40 parts of acetonitrile are refluxed together for 24 hours. Upon addition of diisopropyl ether to the reaction mixture, a 1-[2,4-dichloro-β-(2,4-dichlorobenzyloxy)phenethyl]-3-[N-ethyl-N-(2,6-xylyl)carbamoylmethyl-]imidazolium chloride product precipitates as a crystalline solid. After recrystallization from 4-methyl-2-pentanone, the product monohydrate has a melting point of 141° C.

EXAMPLE XXVI 4.2 parts of 1-[2,4-dichloro-β-(2,4-dichlorobenzyloxy)phenethyl]imidazole and 2.2 parts of 2-phenoxyethyl bromide are mixed together in 24 parts of acetonitrile and the resulting mixture is stirred and refluxed overnight. Thereafter, the mixture is diluted with diisopropyl ether and allowed to cool whereupon the desired 1-[2,4-dichloro-β-(2,4-dichlorobenzyloxy)-phenethyl]-3-(2-phenoxyethyl)imidazolium bromide product precipitates as a crystalline solid.

The crude solid product after recovery by filtration is purified by dissolving in chloroform, stirring the chloroform solution with 1 part silicon dioxide for about 10 minutes, filtering off the silicon dioxide, and vaporizing off the solvent under reduced pressure to recover a purified product as residue. The latter after further purification by triturating in a mixture of 4-methyl-2-pentanone and diisopropyl ether and drying is obtained as a hydrate of m.p. 113.2° C.

EXAMPLE XXVII

In a reaction carried out in a manner similar to that described in Example XXVI, 1-[2,4-dichloro-β-(2,4-dichlorobenzyloxy)phenethyl]-3-(m-methoxyphenacyl)imidazolium bromide is prepared by refluxing together 4.2 parts of 1-[2,4-dichloro-β-(2,4-dichlorobenzyloxy)-phenethyl]imidazole, 2.5 parts of 2-bromo-m-methoxyacetophenone in 40 parts of acetonitrile. The product after purification by treating a chloroform solution thereof with silicon dioxide, followed by triturating in 4-methyl-2-pentanone has a m.p. of 177° C.

EXAMPLE XXVIII

In operations carried out in a manner similar to those described in Examples XXVI and XXVII, the following compounds are prepared:

1-[2,4-dichloro-β-(2,4-dichlorobenzyloxy)phenethyl]-3-[N-(2,5-dichlorophenyl)carbamoylmethyl-]imidazolium chloride; m.p. 137.8° C., by the reaction of 1-[2,4-dichloro-β-(2,4-dichlorobenzyloxy)phenethyl]imidazole and 2,2',5'-trichloroacetanilide.

1-[2,4-dichloro-β-(2,4-dichlorobenzyloxy)phenethyl]-3-[N-(2,6-xylyl)carbamoylmethyl]imidazolium chloride hydrate, m.p. 143°–150° Co., by the reaction of 1-[2,4-dichloro-β-(2,4-dichlorobenzyloxy)phenethyl]imidazole and 2-chloroaceto-2',6'-xylidide.

1-[2,4-dichloro-β-(2,4-dichlorobenzyloxy)phenethyl]-3-[N-(3,4-dichlorophenyl)carbamoylmethyl]imidazolium chloride hydrate, m.p. 117°–200° C., by the reaction of 1-[2,4-dichloro-β-(2,4-dichlorobenzyloxy)phenethyl]imidazole and 2,2',4'-trichloroacetanilide, purification as above described followed by recrystallization from ethanol-water.

EXAMPLE XXIX

In a similar manner 4.2 parts of 1-[2,4-dichloro-β-(2,4-dichlorobenzyloxy)phenethyl]imidazole, 2.2 parts of 2-chloro-4'-fluoroacetanilide and 24 parts of acetonitrile are stirred at reflux temperature for 12 hours to obtain a 1-[2,4-dichloro-β-(2,4-dichlorobenzyloxy)phenethyl]-3-[N-(p-fluorophenyl)carbamoylmethyl]imidazolium chloride product which is recovered by diluting the reaction mixture with diisopropyl ether and filtering the precipitated crystalline solid. The product is purified by (a) treating a chloroform solution thereof with charcoal in a manner similar to the silicon dioxide purification of Example XXVI, and (b) triturating with 4-methyl-2-pentanone and diisopropyl ether to obtain a purified product of m.p. 180°–181° C.

EXAMPLE XXX

In reactions carried out in a manner similar to those previously described and employing procedure for recovery of product similar to that described in Examples XXIII to XXIX, and further employing column chromatography as described in Example XI as a step in purification together with trituration in 4-methyl-2-pentanone or ether or mixtures thereof, the following compounds are prepared:

1-[2,4-dichloro-β-(2,4-dichlorobenzyloxy)phenethyl]-3-[N-(o-phenoxyphenyl)carbamoylmethyl]imidazolium chloride hydrate, m.p. 117.2° C., from 1-[2,4-dichloro-β-(2,4-dichlorobenzyloxy)phenethyl]imidazole and 2-chloro-2'-phenoxyacetanilide.

1-(5-chloro-2-thenoylmethyl)-3-[2,4-dichloro-β-(2,4-dichlorobenzyloxy)phenethyl]imidazolium bromide, m.p. 200° C., from 1-[2,4-dichloro-β-(2,4-dichlorobenzyloxy)phenethyl]imidazole and bromomethyl 5-chloro-2-thienyl ketone.

1-[2,4-dichloro-β-(2,4-dichlorobenzyloxy)phenethyl]-3-(2-thenoylmethyl)imidazolium bromide, m.p. 171.3° C., from 1-[2,4-dichloro-β-(2,4-dichlorobenzyloxy)phenethyl]imidazole and bromomethyl 2-thienyl ketone.

1-[2,4-dichloro-β-(2,4-dichlorobenzyloxy)phenethyl]-3-[3-(p-fluorobenzoyl)propyl]imidazolium iodide, m.p. 158.7° C., from 1-[2,4-dichloro-β-(2,4-dichlorobenzyloxy)phenethyl]imidazole and 4-iodo-4'-fluorobutyrophenone.

In a similar operation using 3% methanol in chloroform as eluant in the chromatographic separation step, 1-[2,4-dichloro-β-(2,4-dichlorobenzyloxy)phenethyl]-3-(diphenylmethyl)imidazolium chloride hydrate, m.p. 127.2° C., from 1-[2,4-dichloro-β-(2,4-dichlorobenzyloxy)phenethyl]imidazole and diphenylmethyl chloride.

In a similar operation using 10% methanol in chloroform as eluant in the chromatographic purification step, 1-[2,4-dichloro-β-(2,4-dichlorobenzyloxy)phenethyl]-3-(p-sulfamoylphenethyl)imidazolium iodide, m.p. 172.7° C. by the reaction for 24 hours of 1-[2,4-dichloro-β-(2,4-dichlorobenzyloxy)phenethyl]imidazole and p-(2-iodoethyl)benzenesulfonamide.

EXAMPLE XXXI 4.2 parts of 1-[2,4-dichloro-β-(2,4-dichlorobenzyloxy)-phenethyl]imidazole and 2.2 parts of 2,2'-dichloroacetanilide are mixed together in 24 parts of acetonitrile and the resulting mixture is stirred at reflux temperature overnight. Thereafter, the mixture is allowed to cool, diluted with diisopropyl ether and three drops of water are added, whereupon the desired 1-[N-(o-chlorophenyl)-carbamoylmethyl]-3-[2,4-dichloro-β-(2,4-dichlorobenzyloxy)phenethyl]imidazolium chloride product is precipitated. The crude product thus-obtained is recovered by filtration and purified by (a) stirring a chloroform solution thereof with 1 part of silicon dioxide and activated charcoal, (b) filtering to remove the clarifying agents, (c) vaporizing off the solvent to recover the product as residue, and (d) recrystallizing from 4-methyl-2-pentanone. The purified product has a m.p. of 110.7° C.

EXAMPLE XXXII 4.2 parts of 1-[2,4-dichloro-β-(2,4-dichlorobenzyloxy)phenethyl]imidazole, 3.1 parts of 2-(p-bromophenoxy)ethyl bromide and 24 parts of acetonitrile are stirred together overnight at reflux temperature to obtain the desired 1-[2-(p-bromophenoxy)ethyl]-3-[2,4-dichloro-β-(2,4-dichlorobenzyloxy)phenethyl]imidazolium bromide product. The product is recovered from the reaction mixture by (a) diluting the latter with diisopropyl ether (b) adding three drops of water to precipitate the product as a crystalline solid, and (c) filtering off the precipitated solid. After purification by recrystallization from a mixture of 4-methyl-2-pentanone and diisopropyl ether, the product has a melting point of 131.5°–132.5° C.

EXAMPLE XXXIII

In a similar operation and employing recovery techniques similar to Example XXXII, but employing different amounts of reactants or different purification techniques as indicated, the following compounds are prepared:

1-[2,4-dichloro-β-(2,4-dichlorobenzyloxy)phenethyl]-3-[N-(2,5-dimethoxyphenyl)carbamoylmethyl]imidazolium chloride monohydrate, m.p. 121.1° C., by (a) refluxing for 2 days, 4.2 parts of 1-[2,4-dichloro-β-(2,4-dichlorobenzyloxy)phenethyl]imidazole, 2.5 parts of 2-chloroaceto-2',5'-dimethoxyanilide and 40 parts of acetonitrile, (b) recovering as in Example XXXII, and (c) washing the crude product with ether.

1-[2,4-dichloro-β-(2,4-dichlorobenzyloxy)phenethyl]- 3-[1-(p-toluoyl)ethyl]imidazolium bromide, m.p. 160.4° C., by (a) refluxing together for 72 hours 4.2 parts of 1-[2,4-dichloro-β-(2,4-dichlorobenzyloxy)phenethyl]imidazole, 2.5 parts of 2-bromo-4'-methylpropiophenone and 40 parts of acetonitrile, (b) recovering as in Example XXXII, and (c) purifying by a silicon dioxide treatment of a chloroform solution thereof as described in Example XXVI, followed by triturating in a mixture of 4-methyl-2-pentanone and diisopropyl ether.

1-[2,4-dichloro-β-(2,4-dichlorobenzyloxy)phenethyl]-3-(p-sulfamoylbenzyl)imidazolium bromide hydrate, m.p. 148.3° C. in yield of 4.8 parts, by (a) refluxing together 4.2 parts of 1-[2,4-dichloro-β-(2,4-dichlorobenzyloxy)phenethyl]imidazole and 2.8 parts of p-(bromomethyl)benzenesulfonamide for 24 hours, (b) recovering as in Example XXXII, and (c) purifying by washing with 4-methyl-2-pentanone, followed by chromatographic adsorption with 10% methanol in chloroform, and triturating in 4-methyl-2-pentanone.

EXAMPLE XXXIV 7.34 parts of 1-[p-chloro-β-(p-chlorobenzyloxy)-phenethyl]imidazole and 4.7 parts of o-nitrobenzyl bromide are stirred together at reflux temperature for 20 hours in 80 parts of acetonitrile. Thereafter, the solvent is evaporated off under reduced pressure and there is recovered a 1-[p-chloro-β-(p-chloro-benzyloxy)phenethyl]-3-(o-nitrobenzyl)imidazolium bromide product as residue. The residue is crystallized from a mixture of acetone and diisopropyl ether which after filtering and drying amounted to 10 parts of a purified product having a melting point of 150.3° C.

EXAMPLE XXXV

In a manner similar to that described in Example XXXIV, 1- 1-[N-(2-chloro-6-methylbenzyl)carbamoyl]ethyl -3-[β-(p-chlorobenzyloxy)-2,4-dichlorophenethyl]imidazolium bromide, m.p., 183.1° C., yield 9 parts, is prepared by refluxing together 7.6 parts of 1-[2,4-dichloro-β-(p-chlorobenzyloxy)phenethyl]imidazole and 6.4 parts of 2-bromo-N-(2-choro-6-methylbenzyl)propionamide in 80 parts of acetonitrile for 20 hours, thereafter evaporating off the solvent and crystallizing the residue from a mixture of acetone and diisopropyl ether.

EXAMPLE XXXVI

In a manner similar to that described in Examples XXXIV and XXXV, the following compounds are prepared by refluxing together for from about 12 to about 24 hours, the appropriate imidazole and appropriate halo compound, 80 parts of acetonitrile, thereafter evaporating off the solvent and crystallizing the residue from a mixture of acetone and diisopropyl ether (or as otherwise indicated).

1-[p-Chloro-β-(p-chlorobenzyloxy)phenethyl]-3-[N-(p-fluorophenyl)carbamoylmethyl]imidazolium chloride, m.p. 188° C. in a yield of 10 parts by the reaction of 7.34 parts of 1-[p-chloro-β-(p-chlorobenzyloxy)-phenethyl]imidazole and 4.1 parts of 2-chloroaceto-p-fluoroanilide.

1-(N-Benzylcarbamoylmethyl)-3-[β-(p-chlorobenzyloxy)-2,4-dichlorophenethyl]imidazolium chloride, m.p. 143° C., yield 9 parts, by the reaction of 7.6 parts of 1-[2,4-dichloro-β-(p-chlorobenzyloxy)phenethyl]imidazole and 4 parts of 2-chloro-N-benzylacetamide.

1-(N-Benzylcarbamoylmethyl)-3-[2,4-dichloro-β-(2,4-dichlorobenzyloxy)phenethyl]imidazolium chloride, m.p. 169.4° C., yield 7 parts, by the reaction of 1-[2,4-dichloro-β-(2,4-dichlorobenzyloxy)phenethyl]imidazole and 2-chloro-N-benzylacetamide.

1-(N-Benzyl-N-tert.-butylcarbamoylmethyl)-3-[2,4-dichloro-β-(2,4-dichlorobenzyloxy)phenethyl]imidazolium chloride hydrate, m.p. 105.1° C., yield 6 parts, by the reaction of 1-[2,4-dichloro-β-(2,4-dichlorobenzyloxy)phenethyl]imidazole and N-benzyl-N-tert.-butyl-2-chloroacetamide.

1-[N-(o-Chlorobenzyl)carbamoylmethyl]-3-[2,4-dichloro-β-(2,4-dichlorobenzyloxy)phenethyl]imidazolium chloride, m.p. 147.3° C., yield 8 parts, by the reaction of 8 parts of 1-[2,4-dichloro-β-(2,4-dichlorobenzyloxy)phenethyl]imidazole and 5.2 parts of 2-chloro-N-(o-chlorobenzyl)acetamide.

1-[2,4-Dichloro-β-(2,4-dichlorobenzyloxy)phenethyl]-3-[N-methyl-N-(2,6-xylyl)carbamoylmethyl]imidazolium chloride, m.p. 203° C., yield 7 parts, by the reaction of 8.3 parts of 1-[2,4-dichloro-β-(2,4-dichlorobenzyloxy)phenethyl]imidazole and 4.3 parts of 2-chloroaceto-N-methyl-2',6'-xylidide and in addition recrystallized from 4-methyl-2-pentanone and 2-propanol.

1-[2,4-Dichloro-β-(2,4-dichlorobenzyloxy)phenethyl]-3-[1-(N-phenylcarbamoyl)ethyl]imidazolium bromide, m.p. 187.6° C., yield 6.5 parts, by the reaction for 12 hours of 8.3 parts of 1-[2,4-dichloro-β-(2,4-dichlorobenzyloxy)phenethyl]imidazole and 4.6 parts of 2-bromopropionanilide and recrystallized from 4-methyl-2-pentanone.

In a further similar operation but in which acetone alone is used for crystallization, 1-[β-(allyloxy)-2,4-dichlorophenethyl]-3-(p-fluorophenacyl)imidazolium chloride, m.p. 140.9° C., from 1-(β-allyloxy-2,4-dichlorophenethyl)imidazole and 2-chloro-p-fluoroacetophenone.

In still further similar operations but in which 4-methyl-2-pentanone is employed for crystallization, the following compounds are prepared:

1-[2,4-Dichloro-β-(2,4-dichlorobenzyloxy)phenethyl]-3- 1-[N-(2,3-xylyl)carbamoyl]ethyl imidazolium bromide, m.p. 159.4° C., yield 13 parts, from 8.3 parts of 1-[2,4-dichloro-β-(2,4-dichlorobenzyloxy)phenethyl]imidazole and 5.1 parts of 5-bromo-propiono-2',3'-xylidide.

1-[2,4-Dichloro-β-(2,4-dichlorobenzyloxy)phenethyl]-3-[1-(N-o-tolylcarbamoyl)ethyl]imidazolium bromide, m.p. 139.5° C., yield 11 parts, from 8.3 parts of 1-[2,4-dichloro-β-(2,4-dichlorobenzyloxy)phenethyl]imidazole and 4.8 parts of 2-bromopropiono-o-toluidide.

1-[2,4-Dichloro-β-(p-chlorobenzyloxy)phenethyl]-3-(N-o-tolylcarbamoylmethyl)imidazolium chloride, m.p. 192.8° C., yield 9 parts, from 7.6 parts of 1-[2,4-dichloro-β-(p-chlorobenzyloxy)-phenethyl]imidazole and 4 parts of 2-chloroaceto-o-toluidide.

1-[2,4-Dichloro-β-(p-chlorobenzyloxy)phenethyl]-3-(p-fluorophenacyl)imidazolium chloride, m.p. 163° C., in a yield of 9 parts by the reaction of 7.6 parts of 1-[2,4-dichloro-β-(p-chlorobenzyloxy)phenethyl]imidazole and 3.8 parts of 2-chloro-p-fluoroacetophenone.

1-[2,4-Dichloro-β-(2,6-dichlorobenzyloxy)phenethyl]-3-(p-fluorophenacyl)imidazolium chloride monohydrate, m.p. 139.7° C., yield 5.5 parts from 8.3 parts of 1-[2,4-dichloro-β-(2,6-dichlorobenzyloxy)phenethyl]imidazole and 3.13 parts of 2-chloro-p-fluoroacetophenone.

In a further similar operation but in which diisopropyl ether is employed for crystallization, 1- 1-[N-(2-chloro-6-methylbenzyl)carbamoyl]ethyl -3-[2,4-dichloro-β-(2,4-dichlorobenzyloxy)phenethyl]imidazolium bromide, m.p. 189.8° C., yield 11 parts, from 8 parts of 1-[2,4-dichloro-β-(2,4-dichlorobenzyloxy)phenethyl]imidazole and 6.4 parts of 2-bromo-N-(2-chloro-6-methylbenzyl)propionamide.

EXAMPLE XXXVII 6.3 Parts of 1-(β-butoxy-2,4-dichlorophenethyl)-imidazole and 5.1 parts of (p-chlorophenyl) (p-fluorophenyl)methyl chloride are mixed together in 80 parts of acetonitrile and the resulting mixture is stirred at reflux temperature overnight. Thereafter, the solvent is vaporized off to obtain as residue a 1-(β-butoxy-2,4-dichlorophenethyl)-3-[p-chloro-α-(p-fluorophenyl)-benzyl]imidazolium chloride product.

The crude product is purified by crystallizing from a mixture of 4-methyl-2-pentanone and diisopropyl ether. The purified product has a melting point of 167.5° C.

EXAMPLE XXXVIII

In operations similar to that described in Example XXXVII, 1-[2,4-dichloro-β-(2,6-dichlorobenzyloxy)-phenethyl]-3-(2-phenoxyethyl)imidazolium bromide, m.p. 153.4° C., yield 11 parts, is prepared by refluxing together overnight 8.3 parts of 1-[2,4-dichloro-β-(2,6-dichlorobenzyloxy)phenethyl]imidazole and 4.02 parts of 2-bromoethyl phenyl ether in 80 parts of acetonitrile, thereafter, evaporating off the solvent and crystallizing the residue from a mixture of 4-methyl-2-pentanone and diisopropyl ether.

EXAMPLE XXXIX

In operations similar to that described in Examples XXXVII and XXXVIII, the following compounds are prepared by refluxing together the indicated amounts of the appropriate imidazole and appropriate halo compound in 80 parts of acetonitrile for a period ranging from overnight to about twenty four hours, thereafter evaporating off the solvent and crystallizing the residue thus obtained from a mixture of 4-methyl-2-pentanone and diisopropyl ether:

1-(β-Butoxy-2,4-dichlorophenethyl)-3-(o-nitrobenzyl)imidazolium bromide, m.p. 134° C., yield 10 parts, by the reaction of 6.3 parts of 1-(β-butoxy-2,4-dichlorophenethyl)imidazole and 4.4 parts of o-nitrobenzyl bromide.

1-(β-Butoxy-2,4-dichlorophenethyl)-3-[N-(p-fluorophenyl)-carbamoylmethyl]imidazolium chloride, m.p. 118.5° C., yield 9 parts, by the reaction of 6.3 parts of 1-(β-butoxy-2,4-dichlorophenethyl)-imidazole and 3.8 parts of 2-chloro-4'-fluoroacetanilide.

1- 1-[N-(p-Chlorobenzyl)carbamoyl]ethyl -3-[2,4-dichloro-β-(2,4-dichlorobenzyloxy)phenethyl-]imidazolium bromide; m.p. 162.1° C., yield 3 parts, by the reaction of 8 parts of 1-[2,4-dichloro-β-(2,4dichlorobenzyloxy)phenethyl]imidazole and 6 parts of 2-bromo-N-(p-chlorobenzyl)propionamide.

1-[1-(N-Benzylcarbamoyl)ethyl]-3-[2,4-dichloro-β-(2,4-dichlorobenzyloxy)phenethyl]imidazolium bromide, m.p. 135.9° C., yield 10 parts, by the reaction of 8 parts of 1-[2,4-dichloro-β-(2,4-dichlorobenzyloxyphenethyl]imidazole and 5.3 parts of 2-bromo-N-benzylpropionamide.

1-[2,4-Dichloro-β-(2,4-dichlorobenzyloxy)phenethyl]-3- 1-[N-(p-methoxybenzyl)carbamoyl]ethyl imidazolium bromide, m.p. 136° C., yield 8 parts, by the reaction of 8 parts of 1-[2,4-dichloro-β-(2,4-dichlorobenzyloxy)phenethyl]imidazole and 5.9 parts of 2-bromo-N-(p-methoxybenzyl)propionamide.

1-[2-(p-bromobenzoyl)ethyl]-3-[2,4-dichloro-β-(2,4-dichlorobenzyloxy)phenethyl]imidazolium chloride, m.p. 161.5° C., yield 11.5 parts, by the reaction of 8.3 parts of 1-[2,4-dichloro-β-(2,4-dichlorobenzyloxy)phenethyl]imidazole and 5 parts of 4'-bromo-3-chloropropiophenone.

1-[2,4-Dichloro-β-(2,4-dichlorobenzyloxy)phenethyl]-3-[N-(p-methylbenzyl)carbamoylmethyl-]imidazolium chloride, m.p. 135.2° C., yield 8.5 parts, by the reaction of 8 parts of 1-[2,4-dichloro-β-(2,4-dichlorobenzyloxy)phenethyl]imidazole and 4 parts of 2-chloro-N-(p-methylbenzyl)acetamide.

1-[β-(Allyloxy)-2,4-dichlorophenethyl-]3-[N-(p-fluorophenyl)carbamoylmethyl]imidazolium chloride, m.p. 144.6° C., yield 6.7 parts, by the reaction of 6 parts of 1-(β-allyloxy-2,4-dichloro-phenethyl-)imidazole and 4.2 parts of 2-chloroaceto-p-fluoroanilide.

1-[β-(Allyloxy)-2,4-dichlorophenethyl]-3-(2,4-dichlorobenzyl)imidazolium chloride hydrate, m.p. 89.1° C. yield 7 parts, by the reaction of 6 parts of 1-(β-allyloxy-2,4-dichlorophenethyl)imidazole and 4.3 parts of 2,4-dichlorobenzyl chloride.

1-[p-Chloro-β-(p-chlorobenzyloxy)phenethyl]-3-(N-o-tolylcarbamoylmethyl)imidazolium chloride, m.p. 128.6° C., yield 2.5 parts, by the reaction of 7.34 parts of 1-[p-chloro-β-(p-chlorobenzyloxy)phenethyl-]imidazole and 4 parts of 2-chloroaceto-o-toluidide.

1-[β-(p-Chlorobenzyloxy)-2,4-dichlorophenethyl]-3-(p-chloro-β-hydroxyphenethyl)imidazolium bromide hydrate, m.p. 97.5° C., yield 2 parts, by the reaction of 7.6 parts of 1-[β-(p-chlorobenzyloxy)-2,4-dichlorophenethyl]imidazole and 5.1 parts of α-(bromomethyl)-p-chlorobenzyl alcohol.

In the compounds of the following examples, the products of the designated melting points are obtained after a further step of recrystallization from 4-methyl-2-pentanone.

1- 1-[N-(m-Chlorophenyl)carbamoyl]ethyl -3-[2,4-dichloro-β-(2,4-dichlorobenzyloxy)phenethyl-]imidazolium bromide, m.p. 176° C., from 1-[2,4-dichloro-β-(2,4-dichlorobenzyloxy)phenethyl-]imidazole and 2-bromo-propiono-3'-chloroanilide.

1-[p-Chloro-β-(p-chlorobenzyloxy)phenethyl]-3-(p-fluorophenacyl)imidazolium chloride, m.p. 152.8° C., in a yield of 6 parts, by the reaction of 7.3 parts of 1-[p-chloro-β-(p-chloroenzyloxy)phenethyl]imidazole and 3.8 parts of chloromethyl p-fluorophenylketone.

In the following examples, the crystals obtained are further recrystallized from 4-methyl-2-pentanone:

1-[2,4-Dichloro-β-(p-chloroenzyloxy)phenethyl]-3-[N-p-fluorophenyl)carbamoylmethyl]imidazolium chloride, m.p. 179.4° C., from 1-[2,4-dichloro-β-(p-chlorobenzyloxy)phenethyl]imidazole and 2-chloro-4-fluoroacetanilide.

1-[2,4-Dichloro-β-(2,4-dichlorobenzyloxy)phenethyl]-3-[N-(p-methoxybenzyl)carbamoylmethyl-]imidazolium chloride hydrate, m.p. 124.8° C., from 1-[2,4-dichloro-β-(2,4-dichlorobenzyloxy)-phenethyl-]imidazole and 2-chloro-N-(p-methoxybenzyl)acetamide.

EXAMPLE XL

In a similar manner, 1-[β-(allyloxy)-2,4-dichlorophenethyl]-3-(N-o-tolycarbamoylmethyl)imidazolium chloride, m.p. 205° C., yield 7.3 parts, is prepared from 6 parts of 1-(β-allyloxy-2,4-dichlorophenethyl-)imidazole and 4.1 parts of 2-chloroaceto-o-toluidide, followed by crystallization of solid residue from a mixture of 4-methyl-2-pentanone and methanol.

EXAMPLE XLI

In operations similar to that described in Example XL, the following compounds are prepared and crystallized from a mixture of 4-methyl-2-pentanone and methanol or ethanol:

1-[2,4-Dichloro-β-(2,6-dichlorobenzyloxyl)phenethyl]-3-(o-nitrobenzyl)imidazolium bromide, m.p. 131.2° C., yield 8 parts, by the reaction of 8.3 parts of 1-[2,4-dichloro-β-(2,6-dichlorobenzyloxy)phenethyl]imidazole and 4.2 parts of o-nitrobenzyl bromide.

1-(2,4-Dichlorobenzyl)-3-[2,4-dichloro-β-(2,6-dichlorobenzyloxy)phenethyl]imidazolium chloride, m.p. 201.2° C., yield 8 parts, by the reaction of 8.3 parts of 1-[2,4-dichloro-β-(2,6-dichlorobenzyloxy)-phenethyl]imidazole and 3.91 parts of 2,4-dichlorobenzyl chloride.

EXAMPLE XLII

In operations carried out in a manner similar to that described in Example XXXVII, the following compounds are prepared by refluxing together the appropriate imidazole compound and appropriate halo compound in acetonitrile solvent in the amounts and for the time indicated, thereafter evaporating off the solvent and purifying the residue thus obtained by triturating with a mixture of 4-methyl-2-pentanone and an ether:

1-[2-(p-Chlorobenzoyl)ethyl]-3-[2,4-dichloro-β-(2,4-dichlorobenzyloxy)phenethyl]imidazolium chloride, m.p. 176.2° C., yield 11 parts, from 8.3 parts of 1-[2,4-dichloro-β-(2,4-dichlorobenzyloxy)phenethyl]imidazole and 4 parts of 3,4'-dichloropropiophenone in 80 parts acetonitrile after 12 hours reflux.

1-[2,4-Dichloro-β-(2,4-dichlorobenzyloxy)phenethyl]-3-]N-(α,α,α-trifluoro-m-tolyl)carbamoylmethyl]imidazolium chloride hydrate, m.p. 97.7° C., yield 4.4 parts, from 4.2 parts of 1-[2,4-dichloro-β-(2,4-dichlorobenzyloxy)phenethyl]imidazole and 2.7 parts of 2-chloro-α,α,α-trifluoroaceto-m-toluidide in 40 parts of acetonitrile after an overnight reflux.

1-[2,4-Dichloro-β-(2,4-dichlorobenzyloxyl)phenethyl]-3-[3-(p-fluorophenoxy)propyl]imidazolium bromide, m.p. 117°–140° C. (dec.), yield 4.8 parts, from 4.2 parts of 1-[2,4-dichloro-β-(2,4-dichlorobenzyloxy)phenethyl]imidazole and 2.6 parts of 1-bromo-3-(p-fluorophenoxy)propane in 40 parts of acetonitrile after 20 hour reflux.

In the compounds of the following examples, the products of the designated melting points are obtained after a further step of recrystallization from 4-methyl-2-pentanone or acetonitrile.

1-(p-Chlorophenethyl)-3-[2,4-dichloro-β-(2,4-dichlorobenzyloxy)phenethyl]imidazolium bromide, m.p. 151.1° C., (from 4-methyl-2-pentanone), yield 2.2 parts, by the reaction of 2.5 parts of 1-[2,4-dichloro-β-(2,4-dichlorobenzyloxy)phenethyl]-imidazole and 1.5 parts of p-chlorophenethyl bromide in 40 parts of acetonitrile after 2 days reflux.

1-Cinnamyl-3-[2,4-dichloro-β-(2,4-dichlorobenzyloxy)-phenethyl]imidazolium chloride, m.p. 97°–136.5° C., from 4-methyl2-pentanone), yield 4.3 parts, by the reaction of 4.2 parts of 1-[2,4-dichloro-β-(2,4-dichlorobenzyloxy)phenethyl]imidazole and 2 parts of cinnamyl chloride in 40 parts of acetonitrile after 3 days reflux.

1-[2,4-Dichloro-β-(2,4-dichlorobenzyloxy)phenethyl]-3-[2-(o-tolyoxy)ethyl]imidazolium bromide, m.p. 170°–171° C. (from acetonitrile), by the reaction of 4.2 parts of 1-[2,4-dichloro-β-(2,4-dichlorobenzyloxy)-phenethyl]imidazole and 2.6 parts of 2-(o-methylphenoxy)ethyl bromide in 40 parts of acetonitrile after a 15 hour reflux.

EXAMPLE XLII

In further operations carried out in a manner similar to those described in Example XLII, the following compounds are prepared:

1-[2,4-Dichloro-β-(2,4-dichlorobenzyloxy)phenethyl]-3-dodecylimidazolium bromide, m.p. 75.7° C. yield 4 parts, from 4.2 parts of 1-[2,4-dichloro-β-(2,4d-dichlorobenzyloxy)phenethyl]imidazole and 2.8 parts of n-dodecyl bromide in 24 parts of acetonitrile after an overnight reflux, thereafter evaporating off the solvent and purifying the residue by triturating in diisopropyl ether.

1-[2,4-Dichloro-β-(2,4-dichlorobenzyloxy)-phenethyl]-3- 2-[N-(o-nitrophenyl)carbamoyl]ethyl imidazolium chloride, m.p. 169.1° C., from 1-[2,4-dichloro-β-(2,4-dichlorobenzyloxy)-phenethyl]imidazole and 3-chloropropione-o-nitroanilide by triturating in diisopropyl ether and recrystallizing from 4-methyl-2-pentanone and a mixture of 2-propanol-diisopropyl ether.

1-(o-Chlorobenzyl)-3-[2,4-dichloro-β-(2,4-dichlorobenzyloxy)phenethyl]imidazolium iodide, m.p. 161.8° C., from 1-[2,4-dichloro-β-(2,4-dichlorobenzyloxy)-phenethyl]imidazole and o-chlorobenzyl iodide, and purification by triturating in 2-propanol-ether and recrystallizing from 4-methyl-2-pentanone.

EXAMPLE XLIV

In similar operations, the following compounds are prepared by refluxing together for the time indicated, the indicated amounts of the appropriate imidazole and appropriate halo compound in from 24 to 80 parts of acetonitrile solvent, thereafter evaporating off the solvent and purifying the residue thus obtained by the successive steps of (a) chromatographic absorption employing 5% of methanol in chloroform as the eluant, and (b) triturating in ether or a mixture of 4-methyl-2-pentanone and an ether, with further trituration or crystallization if necessary:

1-[p-Chloro-α-(p-fluorophenyl)benzyl[-3-[2,4-dichloro-β-(2,4-dichlorobenzyloxy)phenethyl]imidazolium chloride, m.p. 154°–162° C., yield 2.2 parts, from 4.2 parts of 1-[2,4-dichloro-β-(2,4-dichlorobenzyloxy)phenethyl]imidazole and 2.8 parts of α-chloro-(p-chlorophenyl) (p-fluorophenyl)methane after an overnight reflux.

1-(p-Chloro-α-propylbenzyl)-3-[2,4-dichloro-β-(2,4-dichlorobenzyloxy)phenethyl]imidazolium bromide, m.p. 151.1° C., yield 2,8 parts, from 4.2 parts of 1-[2,4-dichloro-β-(2,4-dichlorbenzyloxy)phenethyl]imidazole and 1-bromo-1-(p-chlorophenyl)butane after an overnight reflux.

1-[2,4-Dichloro-β-(2,4-dichlorobenzyloxy)phenethyl]3-[2-(m-tolyloxy)ethyl]imidazolium bromide, m.p. 103.1° C., yield 4.1 parts, from 4.2 parts of 1-[2,4-dichloro-β-(2,4-dichlorobenzyloxyl)phenethyl]imidazole and 2-bromoethyl-m-tolyl ether after refluxing for three days.

1-[2-(p-Chlorophenoxy)ethyl]-3-[2,4-dichloro-β-(2,4-dichlorobenzyloxy)phenethyl]imidazolium bromide, m.p. 129.1° C., from 4.2 parts of 1-[2,4-dichloro-β-(2,4-dichlorobenzyloxy)phenethyl]imidazole and 2.6 parts of 2-(p-chlorophenoxy)ethyl bromide after refluxing for two days.

1-(1-Benzoylbutyl)-3-[2,4-dichloro-β-(2,4-dichlorobenzyloxy)phenthyl]imidazolium bromide, m.p. 102.7° C., from 1-[2,4-dichloro-β-(2,4- dichlorobenzyloxy)phenethyl]-imidazole and 2-bromovalerophenone.

1-[2,4-Dichloro-β-(2,4-dichlorobenzyloxy)phenethyl]-3-(p-fluoro-α-phenylbenzyl)imidazolium chloride, m.p. 199°–201° C., yield 2.5 parts, from 4.2 parts of 1-[2,4-dichloro-β-(2,4-dichlorobenzyloxy)phenethyl]imidazole and 2.5 parts of α-chloro-4-fluorodiphenylmethane after an overnight reflux.

In further similar operations, except that the eluant in the chromatographic purification step was 3% methanol in chloroform, the following compound is prepared:

1-[2,4-Dichloro-β-(2,4-dichlorobenzyloxy)phenethyl]-3-(5-fluoro-2,3-dihydro-2-benzofuranylmethyl)imidazolium bromide hydrate, m.p. 91.6° C., from 4.2 parts of 1-[2,4-dichloro-β(2,4-dichlorobenzyloxy)phenethyl]imidazole and 2.6 parts of 2-bromomethyl-5-fluoro-2,3-dihydrobenzofuran after 3day reflux.

In still further similar operations, but employing 10% methanol in chloroform as eluant, the following compounds are prepared:

1-[2,4-Dichloro-β-(2,4-dichlorobenzyloxy)phenethyl]-3-[bis-(p-fluorophenyl)methyl]imidazolium chloride, m.p. 195.5° C.

1-[2,4-Dichloro-β-(2,4-diclorobenzyloxy)phenethyl]-3-(p-fluorocinnamyl)imidazolium chloride hydrate, m.p. 91.8° C.

EXAMPLE XLV

In similar operations, the following compounds are prepared by refluxing together the appropriate imidazole and approprate halo compound in acetonitrile for from about 12 hours to about 3 days, thereafter evaporating off the solvent and purifying the residue first by (a) washing or triturating, generally in a mixture of ketone and ether, thereafter by (b) column chromatography using a mixture of chloroform and methanol or 4-methyl-2-pentanone and if necessary, followed by further triturating or crystallization:

1-[2,4-Dichloro-β-(2,4-dichlorobenzyloxy)phenethyl]3-(β-hydroxy-m-methoxyphenethyl)imidazolium bromide, m.p. 166° C., from 1-[2,4-dichloro-β-(2,4-dichlorobenzyloxy)phenethyl]-imidazole and β-(bromomethyl)-m-methoxybenzyl alcohol.

1-[2,4-Dichloro-β-(2,4-dichlorobenzyloxy)phenethyl]-3-(3-phenylpropyl)imidazolium bromide, m.p. 153.7° C. from 1-[2,4-dichloro-β-(2,4-dichlorobenzyloxy)phenethyl]imidazole and 3-phenylpropyl bromide.

1-[N-(6-Chloro-o-tolyl)carbamoylmethyl]-3-]2,4-dichloro-β-(2,4-dichlorobenzyloxy)phenethyl-]imidazolium chloride hydrate, m.p. 201.1° C., from 1-[2,4dichloro-β-(2,4-dichlorobenzyloxy)phenethyl-]imidazole and 2,6′-dichloroaceto-o-toluidide.

1-[2,4-Dichloro-β-(2,4-dichlorobenzyloxy)phenethyl]3-(p-methoxyphenacyl)imidazolium bromide, m.p. 173.3° C., by the reaction of 1-[2,4-dichloro-β-(2,4-dichlorobenzyloxy)phenethyl]-imidazole and 2-bromo-4′-methoxyacetophenone.

EXAMPLE XLVI

In operations similar to that previously described, 4.2 parts of 1-[2,4-dichloro-β-(2,4-dichlorobenzyloxy)-phenethyl]imidazole and 3.2 parts of α-bromo-5-nitro-o-tolyl)butyl ether are stirred together and refluxed for 7 hours and 24 parts of acetonitrile solvent and thereafter the solvent removed in vacuo to obtain the desired 1-(2-butoxy-4-nitrobenzyl)-3-[2,4-dichloro-β-(2,4-dichloro-benzyloxy)phenethyl]imidazolium bromide product as residue.

The product is purified (1) by dissolving in chloroform, stirring the chloroform solution with one part of silicon dioxide for about 10 minutes, filtering off the silicon dioxide, then evaporating off the solvent to obtain a residue and (2) triturating the residue in 4-methyl-2-pentanone. The purified product obtained in a yield of 5 parts has a m.p. of 154°–158° C.

EXAMPLE XLVII

In operations carried out in a manner similar to that described in Example XLVI, the following compounds are prepared by refluxing together the appropriate imidazole compound and the appropriate halo compound overnight in acetonitrile, thereafter, recovering the product by vaporizing off the solvent and purifying the product by (a) stirring a chloroform solution thereof with silicon dioxide, followed by (b) triturating in a mixture of 4-methyl-2-pentanone and an ether.

1-[2,4-Dichloro-β-(2,4-dichlorobenzyloxy)phenethyl]-3-(p-fluorophenethyl)imidazolium bromide hydrate, m.p. 101.5°–106° C., yield 4 parts, from 4.2 parts of 1-[2,4-dichloro-β-(2,4-dichlorobenzyloxy)phenethyl]imidazole and 2.2 parts of pfluorophenethyl bromide.

1-[2,4-Dichloro-β-(2,4-dichlorobenzyloxy)phenethyl]-3-[2-(p-fluorophenoxy)ethyl]imidazolium bromide hydrate, m.p. 107°–109° C., yield 4.3 parts, from 4.2 parts of 1-[2,4-dichloro-β-(2,4-dichlorobenzyloxy)phenethyl]imidazole and 2.4 parts of 2-(p-fluorophenoxy)ethyl bromide.

In a further similar operation except that an acetone-water mixture is employed in the trituration step, 1-[2,4-dichloro-β-(2,4-dichlorobenzyloxy)phenethyl]-3-[N-(2,4-dichlorophenyl)-carbamoylmethyl-]imidazolium chloride hydrate, m.p. 118°–122° C., is prepared from 1-[2,4-dichloro-β-(2,4-dichlorobenzyloxy)phenethy]imidazole and 2,2′,6′-trichloroacetanilide.

EXAMPLE XLVIII

In further similar operations, the imidazolium salts are obtained by refluxing together for from overnight to 4 days, the appropriate imidazole and appropriate halo compound, recovering and purifying in a manner as described in Examples XLVI and XLVII, but incorporating a trituration or washing step (generally 4-methyl-2-pentanone or 4-methyl-2-pentanone and an ether) prior to silicon dioxide treatment as well as subsequent to it:

1-[2,4-Dichloro-β-(2,4-dichlorobenzyloxy)phenethyl]-3-phenethylimidazolium bromide, m.p. 150.6° C., from 1-[2,4-dichloro-β-(2,4-dichlorobenzyloxy)phenethyl]imidazole and phenethyl bromide.

1-[2,4-Dichloro-β-(2,4-dichlorobenzyloxy)phenethyl]-3-(3,4-dimethylbenzyl)imidazolium chloride, m.p. 137.5° C., from 1-[2,4-dichloro-β-(2,4-dichlorobenzyloxy)phenethyl]imidazole and 3,4-dimethylbenzyl chloride.

1-[2,4-Dichloro-β-(2,4-dichlorobenzyloxy)phenethyl]-3-[2-(p-methoxyphenoxy)ethyl]imidazolium bromide, m.p. 90°–102° C., by the reaction of 1-[2,4-dichloro-β-(2,4-dichlorobenzyloxy)-phenethy]imidazole and 2-(p-methoxyphenoxy)ethyl bromide.

1-[2,4-Dichloro-β-(2,4-dichlorobenzyloxy)phenethyl]-3-(3-phenoxypropyl)imidazolium bromide, m.p.

118° C., by the reaction of 1-[2,4-dichloro-β-(2,4-dichlorobenzyloxy)phenethyl]-imidazole and 3-phenoxypropyl bromide.

EXAMPLE IL

In operations similar to that described in Example XLVIII, the following compound is prepared:

1-[2,4-Dichloro-β-(2,4-dichlorobenzyloxy)phenethyl]-3-[2-(2,4-dichlorophenoxy)ethyl]imidazolium bromide, m.p. 172°–174° C., from 1-[2,4-dichloro-β-(2,4-dichlorobenzyloxy)phenethyl]imidazole and 2-(2,4-dichlorophenoxy)ethyl bromide.

EXAMPLE L

A mixture of 8.3 parts of 1-[2,4-dichloro-β-(2,4-dichlorobenzyloxy)phenethyl]imidazole and 5.1 parts of 2-bromopropiono2',6'-xylidide in 80 pars of acetonitrile is stirred at reflux temperature for 12 hours. At the end of this period the solvent is vaporized off in a manner similar to that previously described to obtain a 1-[2,4-dichloro-β-(2,4-dichlorobenzyloxy)phenethyl]-3- 1-[N-(2,6-xylyl)carbamoyl]ethyl imidazolium bromide product as residue. The latter is purified by boiling twice in diisopropyl ether, decanting the latter each time and then in 4-methyl-2-pentanone to obtain a purified product, m.p. 153.2° C.

EXAMPLE LI

In operations carried out in a manner similar to that described in Example L, the following compounds are prepared from 1-[2,4-dichloro-β-(2,4-dichlorobenzyloxy)phenethyl]imidazole and the appropriate haloamide:

1- 1-[N-(6-Chloro-o-tolyl)carbamoyl]ethyl -3-[2,4-dichloro-β-(2,4-dichlorobenzyloxy)phenethyl-]imidazolium bromide, m.p. 194.3° C.

1- 1-[N-(o-Chlorophenyl)carbamoyl]ethyl -3-[2,4-dichloro-β-(2,4-dichlorobenzyloxy)phenethyl-]imidazolium bromide, m.p. 159.8° C. 1-[2,4-Dichloro-β-(2,4-dichlorobenzyloxy)phenethyl]-3- 1-[N-(2,5-xylyl)carbamoyl]ethyl imidazolium bromide, m.p. 182.2° C.

1- 1-[N-(3-Chloro-p-tolyl)carbamoyl]ethyl -3-[2,4-dichloro-β-(2,4-dichlorobenzyloxy)phenethyl-]imidazolium bromide, m.p. 154.6° C.

In a similar operation but using a mixture of 4-methyl-2-pentanone and diisopropyl ether in the final crystallization, the following compound is prepared:

1-[2,4-Dichloro-β-(2,4-dichlorobenzyloxy)phenethyl]-3-[1-(N-phenethylcarbamoyl)ethyl]imidazolium bromide, m.p. 148.5° C.

EXAMPLE LII

In operations carried out in a manner previously described by heating the appropriate imidazole and the appropriate halo compound in acetonitrile under reflux and purifying the product obtained by a combination of procedures previously described, the following compounds are obtained:

1-[2,4-Dichloro-β-(2,4-dichlorobenzyloxy)phenethyl]-3-[3-(p-tolyoxy)propyl]imidazolium bromide, m.p. 106.1° C.

1-[2,4-Dichloro-β-(2,4-dichlorobenzyloxy)phenethyl]-3-[2-(2,6-xylyloxy)ethyl]imidazolium bromide, m.p. 119.3° C.

EXAMPLE LII 8.3 Parts of 1-[2,4-dichloro-β-(2,4-dichlorobenzyloxy)phenethyl]imidazole and 5.6 parts of 3-chloro-α,α,α-trifluoropropiono-m-toluidide are mixed together and heated overnight at reflux temperature. Thereafter the mixture is evaporated to remove the solvent and to recover a 1-[2,4-dichloro-β-(2,4-dichlorobenzyloxy)phenethyl]-3- 2-[N-(α,α,α-trifluoro-m-tolyl)-carbamoyl]ethyl imidazolium chloride product as residue.

The crude product is purified by (a) column chromatography in the manner described in Example XI but using a mixture of chloroform and 10% methanol as eluant, (b) boiling the residue from the eluate three times in diisopropyl ether, decanting off the ether each time, (c) scratching to solidify the residue, and (d) recrystallizing the solid product from 4-methyl-2-pentanone and diisopropyl ether. The product, after drying for 2 days at 70° C. under reduced pressure amounted to a yield of 5 parts of the product having a melting point of 70.7° C.

EXAMPLE LIV

In operations carried out in a manner similar to that described in Example LIII, the following compounds are prepared from 1-[2,4-dichloro-β-(2,4-dichlorobenzyloxy)phenethyl]imidazole and the appropriate haloanilide:

1-[2,4-Dichloro-β-(2,4-dichlorobenzyloxy)phenethyl]-3- 2-[N-(2,4-dichlorophenyl)carbamoyl]ethyl imidazolium chloride, m.p. 166.5° C.

1-[2,4-Dichloro-β-(2,4-dichlorobenzyloxy)phenethyl]-3-[2-(N-phenylcarbamoyl)ethyl]imidazolium chloride hydrate, m.p. 202.6° C.

1-[2,4-dichloro-β-(2,4-dichlorobenzyloxy)phenethyl]-3- 2-[N-(p-fluorophenyl)carbamoyl]ethyl imidazolium chloride, m.p. 186° C.

1- 2-[N-(4-chloro-o-tolyl)carbamoyl]ethyl -3-[2,4-dichloro-β-(2,4-dichlorobenzyloxy)phenethyl-]imidazolium chloride, m.p. 164° C.

In a further similar operation but employing 1% methanol in chloroform as eluant, the following compound is prepared:

1- 2-[N-(o-Chlorophenyl)carbamoyl]ethyl -3-[2,4-dichloro-β-(2,4-dichlorobenzyloxy)phenethyl-]imidazolium chloride, m.p. 176.2° C.

EXAMPLE LV 4.2 parts of 1-[2,4-dichloro-β-(2,4-dichlorobenzyloxy)-phenethyl]imidazole and 3 parts of 2,4-dichloro-α-(chloromethyl)-benzyl alcohol are mixed together in 40 parts of benzonitrile and the resulting mixture is stirred at reflux temperature for 3 days. At the end of this period the reaction solvent is evaporated off under reduced pressure to obtain a 1-[2,4-dichloro-β-(2,4-dichlorobenzyloxy)phenethyl]-3-(2,4-dichloro-β-hydroxyphenethyl)imidazolium chloride product as residue.

The crude product is purified by (a) column chromatography as previously described using 10% methanol in chloroform as eluant and (b) triturating in a mixture of diisopropyl ether-4-methyl-2-pentanone. The purified product has a melting point of 167.4° C.

EXAMPLE LVI

In operations carried out in a manner similar to that previously described, the following compounds are prepared:

1-[3-(m-Chlorophenoxy)propyl]-3-[2,4-dichloro-β-(2,4-dichlorobenzyloxy)phenethyl]imidazolium methanesulfonate, m.p. 109° C. by stirring together at about 100° C. for 20 hours; 1-[2,4-dichloro-β-(2,4-dichlorobenzyloxy)phenethyl]imidazole and 3-(m-chlorophenoxy)propanol methanesulfonate ester in benzonitrile followed by recovery of the product by vaporizing off the solvent and purification by chromatographic adsorption employing 5% methanol in chloroform as eluant.

1-[2,4-dichloro-β-(2,4-dichlorobenzyloxy)phenethyl]-3-(p-methoxyphenethyl)imidazolium chloride, m.p. 161.8° C., by heating together at about 130° C. for 48 hours, 1-[2,4-dichloro-β-(2,4-dichlorobenzyloxy)-phenethyl]imidazole and p-methoxyphenethyl chloride in benzonitrile, thereafter vaporizing off the solvent and purifying by trituration, chromatographic adsorption and washing.

1-[2,4-Dichloro-β-(2,4-dichlorobenzyloxy)phenethyl]-3-[3-(2-naphthyloxy)propyl]imidazolium chloride hydrate, m.p. 102.5° C., by stirring together at about 140° C. overnight in benzonitrile, 1-[2,4-dichloro-β-(2,4-dichlorobenzyloxy)phenethyl]-imidazole and 3-chloropropyl 2-naphthyl ether, followed by similar recovery and purification procedures.

1-[2,4-Dichloro-β-(2,4-dichlorobenzyloxy)phenethyl]-3-phenethylimidazolium chloride, m.p. 159.2° C., from 1-[2,4-dichloro-β-(2,4-dichlorobenzyloxy)phenethyl]imidazole and phenethyl chloride after an 84 hour reflux, followed by evaporation, recovery and purification which included chromatography using 5% methanol in chloroform as eluant, successive crystallizations from acetone and 4-methyl-2-pentanone, chromatography using chloroform-methanol - methyl ethyl ketone (40:30:30 by volume) as eluant, and crystallization from dioxane.

EXAMPLE LVII 4.2 parts of 1-[2,4-dichloro-β-(2,4-dichlorobenzyloxy)-phenethyl]imidazole and 2.3 parts of 3-chloropropyl phenyl thioether are mixed together and stirred overnight at about 140° C. in 40 parts of benzonitrile. At the end of this period, the reaction mixture is allowed to cool and diisopropyl ether is added, whereupon a 1-[2,4-dichloro-β-(2,4-dichlorobenzyloxy)-phenethyl]-3-[3-(phenylthio)propyl]imidazolium chloride product is precipitated as a crystalline solid which is recovered by filtration.

The product is purified by chromatography employing a mixture of chloroform and 3% of methanol and then by recrystallization from a mixture of 4-methyl-2-pentanone and diisopropyl ether. The purified product is obtained as a sesquihydrate in a yield of 3 parts and with a melting point of 74.6° C.

EXAMPLE LVIII

In reactions and recovery carried out in a manner similar to that described in Example LVII, and purification by chromatography employing a mixture of chloroform and 5% of methanol and by triturating in a mixture of 4-methyl-2-pentanone and diisopropyl ether, the following compound is prepared:

1-[2,4-Dichloro-β-(2,4-dichlorobenzyloxy)phenethyl]-3-[3-(thymyloxy)propyl]imidazolium chloride, m.p. 195.2° C. from 1-[2,4-dichloro-β-(2,4-dichlorobenzyloxy)phenethyl]imidazole and 3-chloropropyl thymyl ether.

EXAMPLE LIX 4.2 Parts of 1-[2,4-dichloro-β-(2,4-dichlorobenzyloxy)-phenethyl]imidazole, 3.5 parts of N-(2-bromoethyl)-p-chloroaniline hydrochloride and 1.7 parts of sodium bicarbonate in 40 parts of acetonitrile are stirred together and heated at reflux temperature for 3 days. At the end of this period, diisopropyl ether is added, whereupon a 1-[2-(p-chloroanilino)ethyl]-3-[2,4-dichloro-β-(2,4-dichlorobenzyloxy)phenethyl]imidazolium bromide product and sodium bromide by-product is precipitated as a crystalline solid.

The product is isolated by filtering to recover the solid mixture, adding chloroform to the mixture to dissolve the imidazolium bromide product, filtering the chloroform medium to remove the sodium bromide by-product, and evaporating off the chloroform. The product residue is triturated in a mixture of 4-methyl-2-pentanone and diisopropyl ether to obtain a purified product of m.p. 140.3° C.

EXAMPLE LX

In operations carried out in a manner similar to that described in Example LIX, the following compounds are prepared:

1-[2-(o-Chloroanilino)ethyl]-3-[2,4-dichloro-β-(2,4-dichlorobenzyloxy)phenethyl]imidazolium bromide, m.p. 181.3° C., by stirring together overnight at reflux temperature 4.2 parts of 1-[2,4-dichloro-β-(2,4-dichlorobenzyloxy)phenethyl]imidazole, 3.5 parts of N-(2-bromoethyl)-o-chloroaniline hydrobromide, 1 part of sodium bicarbonate in 40 parts of acetonitrile, followed by isolation and purification.

1-[2,4-Dichloro-β-(2,4-dichlorobenzyloxy)phenethyl]-3-(2-o-toluidinoethyl)imidazolium bromide, m.p. 152° C., by stirring together at reflux temperature for 3 days, 4.2 parts of 1-[2,4-dichloro-β-(2,4-dichlorobenzyloxy)phenethyl]imidazole, 3.2 parts of N-(2-bromoethyl)-o-toluidine hydrobromide, 1 part of sodium bicarbonate in 40 parts of acetonitrile, followed by isolation and purification.

1-(2-Anilinoethyl)-3-[2,4-dichloro-β-(2,4-dichlorobenzyloxy)phenethyl]imidazolium bromide, m.p. 116° C., by stirring together overnight at reflux temperature 4.2 parts of 1-[2,4-dichloro-β-(2,4-dichlorobenzyloxy)phenethyl]imidazole, 3.1 parts of N-(2-bromoethyl)aniline hydrobromide, 2 parts of sodium bicarbonate in 40 parts of acetonitrile, followed by isolation and purification.

1-[2-(2,6-Dichloroanilino)ethyl]-3-[2,4-dichloro-β-(2,4-dichlorobenzyloxy)phenethyl]imidazolium bromide hydrate, m.p. 120.4° C., by stirring together overnight at reflux temperature, 4.2 parts of 1-[2,4-dichloro-β-(2,4-dichlorobenzyloxy)phenethyl]-imidazole, 3.9 parts of N-(2-bromoethyl)-2',6'-dichloroaniline hydrobromide and 2 parts of sodium bicarbonate in 40 parts of acetonitrile, followed by isolation and purification.

EXAMPLE LXI

In operations similar to that previously described, the following compounds are prepared:

1-[2,4-Dichloro-β-(2,4-dichlorobenzyloxy)phenethyl]-3-[2-(2-naphthyloxy)ethyl]imidazolium bromide hydrate, m.p. 101° C.

1-[p-Chloro-β-(2,4-dichlorobenzyloxy)phenethyl]-3-(N-o-tolylcarbamoylmethyl)imidazolium chloride hydrate, mp. 96.6° C.

1-[β-(Allyloxy)-2,4-dichlorophenethyl]-3-(o-nitrobenzyl)-imidazolium bromide, m.p. 124.3° C.

1-[p-Chloro-β-(2,4-dichlorobenzyloxy)phenethyl]-3-(o-nitrobenzyl)imidazolium bromide, m.p. 174.3° C.

1-Benzyl-3-[β-(p-chlorobenzyloxy)phenethyl]imidazolium bromide, m.p. 126° C.

1- 2-[N-(p-chlorophenyl)-carbamoyl]ethyl -3-[2,4-dichloro-β-(2,4-dichlorobenzyloxy)phenethyl]imidazolium chloride, m.p. 180.5° C.

1-[2,4-Dichloro-β-(2,4-dichlorobenzyloxy)phenethyl]-3-(N-o-tolylcarbamoylmethyl)imidazolium chloride, m.p. 186.5°–191° C.

1-[2,4-Dichloro-β-(2,4-dichlorobenzyloxy)phenethyl]-3-methylimidazolium iodide, m.p. 170° C.

1-[3-(p-Bromophenoxy)-2-oxopropyl]-3-[2,4-dichloro-β-(2,4-dichlorobenzyloxy)phenethyl]imidazolium chloride hydrate, m.p. 126.3° C.

1-[3-(p-Chlorophenoxy)-2-oxopropyl]-3- 2,4-dichloro-β-[(2,4-dichlorobenzyl)oxy]phenethyl imidazolium chloride hydrate, m.p. 136.2° C.

1-[2,4-Dichloro-β-(2,4-dichlorobenzyloxy)phenethyl]-3-[3-(2,4-dichlorophenoxy)-2-oxopropyl]imidazolium chloride dihydrate, m.p. 112.5° C.

EXAMPLE LXII

In further similar operations, the following compounds may be prepared from 1-[β-(p-chlorobenzyloxy)-2,4-dichlorophenethyl]imidazole and the appropriate halo compound:

1-[β-(p-Chlorobenzyloxy-2,4dichlorophenethyl]-3-(p-sulfamoylbenzyl)imidazolium bromide.

1-[β-(p-Chlorobenzyloxy)-2,4-dichlorophenethyl]-3-(cinnamyl)imidazolium chloride.

1-[β-(p-Chlorobenzyloxy)-2,4dichlorophenethyl]-3-[3-(2-naphthyloxy)propyl]imidazolium chloride.

1-(1-Benzoylbutyl)-3-[β-(p-chlorobenzyloxy)-2,4-dichlorophenethyl]imidazolium bromide.

1-[β-(p-Chlorobenzyloxy)-2,4-dichlorophenethyl]-3-[2-(2,6-dichloroanilino)ethyl]imidazolium bromide.

EXAMPLE LXIII

In further similar operations, the following compounds may be prepared:

1-(2-Butoxy-4-nitrobenzyl)-3-[2,4-dichloro-β-(2,6-dichlorobenzyloxy)phenethyl]imidazolium bromide by the reaction of 1-[2,4-dichloro-β-(2,6-dichlorobenzyloxy)phenethyl]imidazole and 2-butoxy-4-nitrobenzyl chloride.

1-(p-Bromo-β-hydroxyphenethyl)-3-[p-chloro-β-(2,4-dichlorobenzyloxy)phenethyl]imidazolium bromide by the reaction of 1-[p-chloro-β-(2,4-dichlorobenzyloxy)phenethyl]imidazole and α-(bromomethyl)-p-bromobenzyl alcohol.

1-(2-Anilinoethyl)-3-[p-chloro-β-(2,4-dichlorobenzyl-oxy)phenethyl]imidazolium bromide by the reaction of 1-[p-chloro-β-(2,4-dichlorobenzyloxy)phenethyl]imidazole and N-(2-bromoethyl)aniline hydrobromide in the presence of sodium bicarbonate.

1-[p-Chloro-β-(p-chlorobenzyloxy)phenethyl]-3-[3-(phenylthio)propyl]imidazolium chloride by the reaction of 1-[p-chloro-β-(p-chlorobenzyloxy)phenethyl]imidazole and 3-chloropropyl phenyl thioether.

1-[2,4-Dichloro-β-(2,6-dichlorobenzyloxy)phenethyl]-3-(n-dodecyl)imidazolium bromide by the reaction of 1-[2,4-dichloro-β-(2,6-dichlorobenzyloxy)phenethyl]imidazole and n-dodecyl bromide.

EXAMPLE LXIV

In further similar operations, the following imidazolium halides may be prepared from 1-(β-allyloxy-2,4-dichlorophenethyl)-imidazole and the appropriate halide compound:

1-[β-(Allyloxy)-2,4-dichlorophenethyl]-3-(cinnamyl)-imidazolium chloride.

1-[β-(Allyloxy)-2,4-dichlorophenethyl]-3-(diphenylmethyl)-imidazolium chloride.

1-[β-(Allyloxy)-2,4-dichlorophenethyl]-3-(2,3-dihydro-2-benzofuranylmethyl)imidazolium bromide.

1-[β-(Allyloxy)-2,4-dichlorophenethyl]-3-(p-bromo-β-hydroxyphenethyl)imidazolium bromide.

1-[β-(Allyloxy)-2,4-dichlorophenethyl]-3-(1-benzoylbutyl)imidazolium bromide.

1-[β-(Allyloxy)-2,4-dichlorophenethyl]-3-[3-(phenylthio)-propyl]imidazolium chloride.

1-[β-(Allyloxy)-2,4-dichlorophenethyl]-3-[2-(2,6-dichloroanilino)ethyl]imidazolium bromide.

In still further similar operations, the following imidazolium halides may be prepared from the appropriate imidazole and the appropriate halide compound:

1-[β-(Allyloxy)-o-chlorophenethyl]-3-(3-phenoxy-2-oxopropyl)imidazolium bromide.

1-[β-(Allyloxy)-o-chlorophenethyl]-3-[3-(p-bromophenoxy)-2-oxopropyl]imidazolium chloride.

1-[β-(Allyloxy)-o-chlorophenethyl]-3-[3-(p-chlorophenoxy)-2-oxopropyl]imidazolium chloride.

1-[β-Allyloxy)-o-chlorophenethyl]-3-[3-(2,4-dichlorophenoxy)-2-oxopropyl]imidazolium chloride.

1-[β-(Allyloxy)-o-chlorophenethyl]-3-[3-(o-fluorophenoxy)-2-oxopropyl]imidazolium chloride.

1-[2,4-Dichloro-β-(2,4-dichlorobenzyloxy)phenethyl]-3-(3-phenoxy-2-oxopropyl)imidazolium bromide.

1-[p-Chloro-β-(p-chlorobenzyloxy)phenethyl]-3-(2,3-dihydro-2-benzofuranylmethyl)imidazolium chloride.

1-[p-Chloro-β-(2,4-dichlorobenzyloxy)phenethyl]-3-(p-iodophenacyl)imidazolium iodide.

1-[2,4-Dichloro-β-(2-butynloxy)-phenethyl]-3-(3-phenoxy-2-oxopropyl)imidazolium bromide.

1-[2,4-Dichloro-β-(2-butynyloxy)phenethyl]-3-[3-(p-bromophenoxy)-2-oxopropyl]imidazolium chloride.

1-[2,4-Dichloro-β-(2-butynyloxy)phenethyl]-3-[3-(p-fluorophenoxy)-2-oxopropyl]imidazolium chloride.

EXAMPLE LXV

In still other similar preparations, the following compounds may be prepared from the appropriate imidazole compound and the appropriate halo compound:

1-(β-Butoxy-2,4-dichlorophenethyl)-3-(5-chloro-2-thenoylmethyl)imidazolium bromide.

1-[2-(p-Bromobenzoyl)ethyl]-3-(β-butoxy-2,4dichlorophenethyl)imidazolium chloride.

1-(β-Butoxy-2,4-dichlorophenethyl)-3-[2-(2,6-xylyloxy)-ethyl]imidazolium bromide.

1-[2-(p-Chloroanilino)ethyl]-3-(β-butoxy-2,4-dichlorophenethyl)imidazolium bromide.

1-(β-Butoxy-2,4-dichlorophenethyl)-3- 1-[N-(o-chlorophenyl)carbamoyl]ethyl imidazolium bromide.

1-(β-Butoxy-2,4-dichlorophenethyl)-3-[N-(p-methoxybenzyl)carbamoylmethyl]imidazolium chloride.

1-(5-Chloro-2-thenoylmethyl)-3-[2,4dichloro-β-(3-pentynyloxy)phenethyl]imidazolium bromide.

1-[2-(p-Bromobenzoyl)ethyl]-3-[2,4-dichloro-β(3-pentynyloxy)phenethyl]imidazolium chloride.

1-[2,4-Dichloro-β-(3-pentynyloxy)phenethyl]-3-[2-(2,6-xylyloxy)ethyl]imidazolium bromide.

1-[2-(p-Chloroanilino)ethyl]-3-[2,4-dichloro-β-(3-pentenyloxy)phenethyl]imidazolium bromide.

1- 1-[N-(o-Chlorophenyl)carbamoyl]ethyl -3-[2,4-dichloro-β-(3-pentenyloxy)phenethyl]imidazolium bromide.

EXAMPLE LXVI

In preparations similar to those described in Example LVI, the following methanesulfonates are prepared:

1-(β-n-Butoxy-2,4-dichlorophenethyl)-3-(5-chloro-2-thenoylmethyl)imidazolium methanesulfonate.

1-[2-(p-Bromobenzoyl)ethyl]-3-(β-butoxy-2,4-dichlorophenethyl)imidazolium methanesulfonate.

1-(β-Butoxy-2,4-dichlorophenethyl)-3-[2-(2,6-xylyloxy)-ethyl]imidazolium methanesulfonate.

1-[2-(p-Chloroanilino)ethyl]-3-(β-butoxy-2,4-dichlorophenethyl)imidazolium methanesulfonate.

1-(β-Butoxy-2,4-dichlorophenethyl)-3- 1-[N-(o-chlorophenyl)carbamoyl]ethyl imidazolium methanesulfonate.

1-(β-Butoxy-2,4-dichlorophenethyl)-3-[N-(p-methoxybenzyl)carbamoylmethyl]imidazolium methanesulfonate.

1-[2,4-Dichloro-β-(3-pentenyloxy)phenethyl]-3-[2-(2,6-xylyloxy)ethyl]imidazolium methanesulfonate.

1-[p-Fluoro-β-(n-propyloxy)phenethyl]-3-phenethylimidazolium methanesulfonate.

1-[β-(p-Chlorobenzyloxy)phenethyl]-3-(p-fluorobenzoylmethyl)imidazolium methanesulfonate.

1-[2,4-Dichloro-β-(3-pentenyloxy)phenethyl]-3-phenethylimidazolium methanesulfonate.

1-(β-Butoxy-2,4-dichlorophenethyl)-3-phenethylimidazolium methanesulfonate.

1-[2-(p-Chloroanilino)ethyl]-3-[2,4-dichloro-β-(3-pentenyloxy)phenethyl]imidazolium methanesulfonate.

EXAMPLE LXVII

In a manner similar to that previously described, the following compounds may be prepared:

1-[β-(p-Chlorobenzyloxy)-2,4-dichlorophenethyl]-3-(n-octyl)imidazolium bromide from 1-[β-(p-chlorobenzyloxy)-2,4-dichlorophenethyl]imidazole and n-octyl bromide.

1-[β-(p-Chlorobenzyloxy)-2,4-dichlorophenethyl]-3- 2-[N-(2,4-dichlorophenyl)carbamoyl]ethyl imidazolium chloride from 1-[β-(p-chlorobenzyloxy)-2,4-dichlorophenethyl]imidazole and 3,2',4'-trichloropropionanilide.

1-[β-(p-Chlorobenzyloxy)-2,4-dichlorophenethyl]-3-[N-methyl-N-(2,6-xylyl)carbamoylmethyl-]imidazolium chloride from 1-[β-(p-chlorobenzyloxy)-2,4-dichlorophenethyl]imidazole and 2-chloroaceto-N-methyl-2',6'-xylidide.

1-[β-(p-Chlorobenzyloxy)-2,4-dichlorophenethyl]-3-[bis-(p-fluorophenyl)methyl]imidazolium chloride from 1-[β-(p-chlorobenzyloxy)-2,4-dichlorophenethyl]imidazole and bis(p-fluorophenyl)chloromethane.

EXAMPLE LXVIII 0.2 Mole of gaseous hydrogen chloride is dissolved in 32 parts of methanol and to this solution are added 12 parts of 1-[2,4-dichloro-β-(2,4-dichlorobenzyloxy)-phenethyl]-3-phenethylimidazolium bromide. The resulting mixture is heated slowly to reflux temperature and stirred at reflux for 1.25 hours. The mixture is then cooled and evaporated, and the residue is triturated in n-hexane. The latter is decanted and the residual oil is boiled in methyl ethyl ketone, whereupon the desired product is precipitated as a solid. The latter is filtered off and crystallized from dioxane to obtain a purified 1-[2,4-dichloro-β-(2,4-dichlorobenzyloxy)phenethyl]-3-phenethylimidazolium chloride product, m.p. 159.5° C.

EXAMPLE LXIX

In a manner similar to that previously described, the following compounds may be prepared:

1-(β-Butoxy-2,4-dichlorophenethyl)-3-(5-chloro-2-thenoylmethyl)imidazolium chloride.

1-[2,4-Dichloro-β-(3,4-dimethylbenzyloxy)phenethyl]-3- 2-[N-(o-nitrophenyl)carbamoyl]ethyl imidazolium chloride.

1-[o-Methyl-β-(p-nitrophenoxy)phenethyl]-3-[N-(p-fluorophenyl)carbamoylmethyl]imidazolium chloride.

1-[2-(phenethyloxy)-2-(2-thienyl)ethyl]-3-[2-(p-tolyloxy)-ethyl]imidazolium bromide.

1-[2-(5-Chloro-2-thienyl)-2-(p-methoxyphenethyloxy)-ethyl]-3-(o-nitrobenzyl)imidazolium bromide.

EXAMPLE LXX

In a manner similar to that described for the methanesulfonates, the following p-toluenesulfonates may be prepared from the appropriate imidazole and the p-toluenesulfonyl ester of the appropriate alcohol:

1-[2,4-Dichloro-β-(2,4-dichlorobenzyloxy)phenethyl]-3-[2-(2-naphthyloxy)ethyl]imidazolium p-toluenesulfonate.

1-[p-Chloro-β-(2,4-dichlorobenzyloxy)phenethyl]-3-[N-(o-tolyl)carbamoylmethyl]imidazolium p-toluenesulfonate.

1-[β-Allyloxy)-2,4-dichlorophenethyl]-3-(o-nitrobenzyl)-imidazolium p-toluenesulfonate.

1-[p-Chloro-β-(2,4-dichlorobenzyloxy)phenethyl]-3-(o-nitrobenzyl)imidazolium p-toluenesulfonate.

1-Benzyl-3-[β-(p-chlorobenzyloxy)phenethyl-]imidazolium p-toluenesulfonate.

1- 2-[N-(p-Chlorophenyl)carbamoyl]ethyl -3-[2,4-dichloro-β-(2,4-dichlorobenzyloxy)phenethyl-]imidazolium p-toluenesulfonate.

1-[3-(p-Chlorophenoxy)-2-oxopropyl]-3-[2,4-dichloro-β-(2,4-dichlorobenzyloxy)phenethyl-]imidazolium p-toluenesulfonate.

EXAMPLE LXXI

A. A mixture of 8.6 parts of 1-(2-phenylethyl)-1H-imidazole, 24.5 parts of 2,4-dichloro-β-(2,4-dichlorophenylmethoxy)benzeneetahanol methanesulfonate and 150 parts of N,N-dimethylformamide is stirred and refluxed overnight. This mixture is allowed to cool to trichloromethane. The combined organic phases are washed three times with water, dried, filtered and evaporated, yielding 1-[2,4-dichloro-β-(2,4-dichlorobenzyloxy)phenethyl]-3-phenethylimidazolium methanesulfonate as an oily residue. The oily residue is taken up in ethanol and brought on an ion exchange column (Amberlite IRA 400) previously converted into the hydroxyl form by treatment with a sodium hydroxide solution. The product in the form of a quaternary imidazolium hydroxide is eluted with ethanol and to the eluate there are added 30 parts of a concentrated hydrochloric acid solution. After evaporating off the solvent there is obtained 1-[2,4-dichloro-β-(2,4-dichlorobenzyloxy)phenethyl]-3-phenethylimidazolium chloride, m.p. 158.9° C.

B. By repeating the procedure of Example LXXI and using therein equivalent amounts of the appropriate starting materials, the following end-products of formula (I) are obtained:

1-[2,4-Dichloro-β-(2,4-dichlorobenzyloxy)phenethyl]-3-(p-fluorobenzoylmethyl)imidazolium chloride; m.p. 180.4° C.

1-(2,4-Dichlorobenzoylmethyl)-3-[2,4-dichloro-β-(2,4-dichlorobenzyloxy)phenethyl]imidazolium chloride; m.p. 185.3° C.

1-[2,4-Dichloro-β-(2,4-dichlorobenzyloxy)phenethyl]-3-(p-methoxyphenethyl)imidazolium chloride; m.p. 161° C.

EXAMPLE LXXII

By repeating the procedure of Example LXXI-A, using therein equivalent amounts of the appropriate starting materials, and by adding to the eluate an equiivalent amount of an appropriate acid in place of the hydrochloric acid used therein, the following compounds are obtained:

1-[2,4-Dichloro-β-(2,4-dichlorobenzyloxy)phenethyl]-3-phenethylimidazolium nitrate.

1-[2,4-Dichloro-β-(2,4-dichlorobenzyloxy)phenethyl]-3-phenethylimidazolium sulfate.

1-[2,4-Dichloro-β-(2,4-dichlorobenzyloxy)phenethyl]-3-phenethylimidazolium phosphate.

1-[2,4-Dichloro-β-(2,4-dichlorobenzyloxy)phenethyl]-3-phenethylimidazolium acetate.

1-[2,4-Dichloro-β-(2,4-dichlorobenzyloxy)phenethyl]-3-phenethylimidazolium cyclohexanesulfamate.

1-[2,4-Dichloro-β-(2,4-dichlorobenzyloxy)phenethyl]-3-phenethylimidazolium propionate.

1-[2,4-Dichloro-β-(2,4-dichlorobenzyloxy)phenethyl]-3-(p-fluorobenzoylmethyl)imidazolium nitrate.

1-[2,4-Dichloro-β-(2,4-dichlorobenzyloxy)phenethyl]-3-(p-fluorobenzoylmethyl)imidazolium sulfate.

1-[2,4-Dichloro-β-(2,4-dichlorobenzyloxy)phenethyl]-3-(p-fluorobenzoylmethyl)imidazolium acetate.

1-(2,4-Dichlorobenzoylmethyl)-3-[2,4-dichloro-β-(2,4-dichlorobenzyloxy)phenethyl]imidazolium nitrate.

1-(2,4-Dichlorobenzoylmethyl)-3-[2,4-dichloro-β-(2,4-dichlorobenzyloxy)phenethyl]imidazolium sulfate.

1-(2,4-Dichlorobenzoylmethyl)-3-[2,4-dichloro-β-(2,4-dichlorobenzyloxy)phenethyl]imidazolium acetate.

1-[2,4-Dichloro-β-(2,4-dichlorobenzyloxy)phenethyl]-3-(p-methoxyphenethyl)imidazolium nitrate.

1-[2,4-Dichloro-β-(2,4-dichlorobenzyloxy)phenethyl]-3-(p-methoxyphenethyl)imidazolium sulfate.

1-[2,4-Dichloro-β-(2,4-dichlorobenzyloxy)phenethyl]-3-(p-methoxyphenethyl)imidazodium acetate.

EXAMPLE LXXIII

In operations carried out in a manner similar to that previously described, the following compounds may be prepared from phenethyl chloride and the appropriate imidazole:

1-[β-(p-Methoxybenzyloxy)phenethyl]-3-phenethylimidazolium chloride.

1-[β-(p-Bromobenzyloxy)phenethyl]-3-phenethylimidazolium chloride.

1-[p-Chloro-β-(3,5-dinitrophenoxy)phenethyl]-3-phenethylimidazolium chloride.

1-[β-(m-Nitrophenoxy)phenethyl]-3-phenethylimidazolium chloride.

1-[2,4-Dibromo-β-(p-cyanobenzyloxy)phenethyl]-3-phenethylimidazolium chloride.

1-[p-Isopropoxy-β-(3,5-dinitrophenoxy)phenethyl]-3-phenethylimidazolium chloride.

1-[p-(n-butyl)-β-(p-cyanobenzyloxy)phenethyl]-3-phenethylimidazolium chloride.

1-[β-(p-Aminophenoxy)phenethyl]-3-phenethylimidazolium chloride.

In further similar operations, the following compounds may be prepared from 2-chloro-4'-fluoroacetophenone and the appropriate imidazole:

1-[2,4-Dichloro-β-(p-bromobenzyloxy)phenethyl]-3-(p-fluorobenzoylmethyl)imidazolium chloride.

1-(β-Benzyloxy-2,3,4-trichlorophenethyl)-3-(p-fluorobenzoylmethyl)imidazolium chloride.

1-[2-Isopropoxy-β-(p-nitrophenoxy)phenethyl]-3-(p-fluorobenzoylmethyl)imidazolium chloride.

1-[4-Ethyl-β-(2,4-dichlorophenethyloxy)phenethyl]-3-(p-fluorobenzoylmethyl)imidazolium chloride.

1-[p-Chloro-β-(2,4,6-trichlorobenzyloxy)phenethyl]-3-(p-fluorobenzoylmethyl)imidazolium chloride.

1-[β-(3,5-Diaminophenoxy)phenethyl]-3-(p-fluorobenzoylmethyl)imidazolium chloride.

1-[2,4-Dichloro-β-(2,4-diethylbenzyloxy)phenethyl]-3-(p-fluorobenzoylmethyl)imidazolium chloride.

EXAMPLE LXXIV

In operations carried out in a manner similar to that described in Example LXXI-A, the following compounds may be prepared:

1-[o-Methyl-β-(p-nitrophenoxy)phenethyl]-3-[N-(p-phenoxyphenyl)carbamoylmethyl]imidazolium glycolate.

1-[o-Ethyl-β-(p-aminophenoxy)phenethyl]-3-[p-isopropoxybenzoylmethyl)imidazolium lactate.

1-(p-Bromo-α-propylbenzyl)-3-[o-methyl-β-(p-aminophenoxy)-phenethyl]imidazolium pyruvate.

1-[β-Allyloxy-o-fluorophenethyl]-3-[3-(p-isopropoxyphenyl)-propyl]imidazolium malonate.

1-[β-(p-Bromobenzyloxy)phenethyl]-3-(3-carvacrylpropyl)imidazolium succinate.

1-[β-(p-Chlorobenzyloxy)phenethyl]-3-(p-bromo-α-propylbenzyl)imidazolium citrate.

1-[β-(p-Chlorobenzyloxy)phenethyl]-3-(2-(o,p-xylidino)-ethyl]imidazolium tartrate.

1-[o-Ethyl-β-(p-nitrophenoxy)phenethyl]-3-[3-(p-chlorophenylthio)propyl]imidazolium maleate.

1-[o-Bromo-β-(p-cyanobenzyloxy)phenethyl]-3-[3-(2-naphthylthio)propyl]imidazolium benzoate.

1-[2,4-Dichloro-β-(p-cyanobenzyloxy)phenethyl]-3-(5-chloro-2,3-dihydro-2-benzofuranylmethyl)imidazolium p-aminosalicylate.

1-[β-(p-Aminophenoxy)phenethyl]-3-(5-bromo-2,3-dihydro-2-benzofuranylmethyl)imidazolium salicylate.

1-[2,4-Dibromo-β-(2,4-dibromobenzyloxy)phenethyl]-3-(2,4-dimethoxy-β-hydroxyphenethyl)imidazolium cinnamate.

1-[2-(5-Chloro-2-thienyl)-2-(p-methoxyphenethyloxy)ethyl]-3-(4-isopropoxy-β-hydroxyphenethyl)imidazolium benzenesulfonate.

1-(p-Bromocinnamyl)-3-[2-(phenethyloxy)-2-(2-thienyl)-ethyl]imidazolium fumarate.

1-(p-Chlorocinnamyl)-3-[2-(phenethyloxy)-2-(2-thienyl)ethyl]imidazolium mandelate.

1-(p-Fluorocinnamyl)-3-[2-(phenethyloxy)-2-(2-thienyl)ethyl] maleate.

1-[β-(p-Methoxybenzyloxy)phenethyl]-3-phenethylimidazolium ethanesulfonate.

1-[2,4-Dichloro-β-(2,4-dichlorobenzyloxy)phenethyl]-3-phenethylimidazolium citrate.

1-[3-(2-Allyl-4-fluorophenoxy)propyl]-3-[2,4-dichloro-β-(2,4-dichlorobenzyloxy)phenethyl]imidazolium malate.

1-Decyl-3-[2,4-dichloro-β-(2,4-dichlorobenzyloxy)phenethyl]imidazolium p-toluenesulfonate.

1-[2,4-Dichloro-β-(2,4-dichlorobenzyloxy)phenethyl]-3-n-octylimidazolium ethanesulfonate.

EXAMPLE LXXV

In operations carried out in a manner similar to that described in the foregoing examples, the following imidazolium salts may be prepared:

1-[β-(Benzyloxy)-2-methylphenethyl]-3-(n-hexyl)-imidazolium nitrate.

1-[β-(Allyloxy)-2-ethoxyphenethyl]-3-(n-heptyl)imidazolium sulfate.

1-[2-(2-Butynyloxy)-2-(5-chloro-2-thienyl)ethyl]-3-(n-decyl)imidazolium phosphate.

1-[2-(2-Butyloxy)-2-(2-thienyl)ethyl]-3-(-n-nonyl)imidazolium acetate.

1-[β-(3,4-Dimethylbenzyloxy)-2-isopropylphenethyl]-3-(-n-undecyl)imidazolium succinate.

1-[β-(Benzyloxy)-2-methylphenethyl]-3-[N-(p-fluorophenyl)carbamoylmethyl]imidazolium ethanesulfonate.

1-[β-(Allyloxy)-2-ethoxyphenethyl]-3-[N-(o-tolyl)-carbamoylmethyl)imidazolium glycolate.

1-[2-(2-Butynyloxy)-2-(5-chloro-2-thienyl)ethyl]-3-1-[N-(p-fluorophenyl)carbamoyl]ethyl imidazolium lactate.

1-[2-(2-Butyloxy)-2-(2-thienyl)ethyl]-3-[N-(2,5-xylyl)carbamoylmethyl]imidazolium pyruvate.

1-[β-(3,4-Dimethylbenzyloxy)-2-isopropylphenethyl]-3- 1-[N-(p-methylbenzyl)carbamoyl]ethyl imidazolium malonate.

1-[β-(p-Cyanophenethyloxy)-4-(n-propoxy)phenethyl]-3-[N-(m-methoxyphenyl)carbamoylmethyl]imidazolium succinate.

1-[β-(2,4-Diaminophenoxy)-2-(2-thienyl)ethyl]-3-[N-(o-methoxyphenyl)carbamoylmethyl]imidazolium maleate.

1-[β-(Benzyloxy)-2-methylphenethyl]-3-(m-methoxyphenacyl)imidazolium fumarate.

1-[β-(Allyloxy)-2-methylphenethyl]-3-(5-chloro-2-thenoylmethyl)imidazolium malate.

1-[2-(2-Butynyloxy)-2-(5-chloro-2-thienyl)ethyl]-3-(2-thenoylmethyl)imidazolium tartrate.

1-[2-(2-Butyloxy)-2-(2-thienyl)ethyl]-3-[3-(p-fluorobenzoyl)propyl]imidazolium citrate.

1-[β-(3,4-Dimethylbenzyloxy)-2-isopropylphenethyl]-3-[1-(p-toluoyl)ethyl]imidazolium benzoate.

1-[β-(p-Cyanophenethyloxy)-4-(n-propoxy)phenethyl]-3-(p-fluorophenacyl)imidazolium cinnamate.

1-[β-(2,4-diaminophenoxy)-2-(2-thienyl)ethyl-3-(p-bromophenacyl)imidazolium mandelate.

1-[β-Benzyloxy)-2-methylphenethyl]-3-(p-fluorobenzyl)imidazolium ethanesulfonate.

1-[β-(Allyloxy)-2-ethoxyphenethyl]-3-(o-nitrobenzyl)imidazolium benzenesulfonate.

1-[2-(2-Butynyloxy)-2-(5-chloro-2-thienyl)ethyl]-3-(m-methylbenzyl)imidazolium cinnamate.

1-[2-(2-Butyloxy)-2-(2-thienyl)ethyl]-3-(p-ethylbenzyl)imidazolium mandelate.

1-[β-(3,4-Dimethylbenzyloxy)-2-isopropylphenethyl]-3-(2-ethoxy-5-nitrobenzyl)imidazolium ethanesulfonate.

1-[β-(p-Cyanophenethyloxy)-4-(n-propoxy)phenethyl]-3-(2-cyano-4-nitrobenzyl)imidazolium cyclohexanesulfamate.

1-[β-(2,4-Diaminophenoxy)-2-(2-thienyl)ethyl]-3-(p-sulfamoylphenethyl)imidazolium phosphate.

1-[β-(Benzyloxy)-2-methylphenethyl]-3-[p-chloro-α-(p-fluorophenyl)benzyl]-imidazolium salicylate.

1-[β-(Allyloxy)-2-ethoxyphenethyl]-3-[bis-(p-fluorophenyl)methyl]imidazolium p-aminosalicylate.

1-[2-(2-Butynyloxy)-2-(5-chloro-2-thienyl)ethyl]-3-[bis-(p-chlorophenyl)methyl]imidazolium propionate.

1-[2-(2-Butyloxy)-2-(2-thienyl)ethyl]-3-(p-fluoro-α-phenylbenzyl)imidazolium acetate.

1-[β-(3,4-Dimethylbenzyloxy)-2-isopropylphenethyl]-3-(p-chloro-α-phenylbenzyl)imidazolium sulfate.

1-[β-(p-Cyanophenethyloxy)-4-(n-propoxy)phenethyl]-3-(p-bromo-α-phenylbenzyl)imidazolium phosphate.

1-[β-(2,4-diaminophenoxy)-2-(2-thienyl)ethyl]-3-(diphenylmethyl)imidazolium nitrate.

1-[β-(Benzyloxy)-2-methylphenethyl]-3-[2-(p-chloroanilino)ethyl]imidazolium methanesulfonate.

1-[β-(Allyloxy)-2-methoxyphenethyl]-3-[2-(o-chloroanilino)ethyl]imidazolium acetate.

1-[2-(2-Butynyloxy)-2-(5-chloro-2-thienyl)ethyl]-3-(2-o-toluidinoethyl)imidazolium glycolate.

1-[2-(2-Butyloxy)-2-(2-thienyl)ethyl]-3-(2-anilinoethyl)-imidazolium lactate.

1-[β-(3,4-Dimethylbenzyloxy)-2-isopropylphenethyl]-3-(2-anilinoethyl)imidazolium pyruvate.

1-[β-(p-Cyanophenethyloxy)-4-(n-propoxy)phenethyl]-3-[2-(p-chloroanilino)ethyl]imidazolium malonate.

1-[β-(2,4-Diaminophenoxy)-2-(2-thienyl)ethyl]-3-[2-(o-bromoanilino)ethyl]imidazolium tartrate.

1-[β-(Benzyloxy)-2-methylphenethyl]-3-[3-(m-chlorophenoxy)propyl]imidazolium citrate.

1-[β-(Allyloxy)-2-ethoxyphenethyl]-3-[3-(2-naphthyloxy)propyl]imidazolium cinnamate.

1-[2-Butynyloxy)-2-(5-chloro-2-thienyl)ethyl]-3-[2-(naphthyloxy)ethyl]imidazolium benzenesulfonate.

1-[2-Propyloxy)-2-(2-thienyl)ethyl]-3-[3-(p-chlorophenoxy)propyl)imidazolium cyclohexanesulfamate.

1-[β-(3,4-Dimethylbenzyloxy)-2-isobutylphenethyl]-3-[3-(phenylthio)propyl]imidazolium salicylate.

1-[β-(p-Cyanophenethyloxy)-4-(n-propoxy)phenethyl]-3-[3-(thymyloxy)propyl]imidazolium sulfate.

1-[β-(2,4-diaminophenoxy)-2-(2-thienyl)ethyl]-3-[3-(phenylthio)propyl]imidazolium nitrate.

1-[β-(Benzyloxy)-2-ethylphenethyl]-3-(5-fluoro-2,3-dihydro-2-benzofuranylmethyl)imidazolium nitrate.

1-[β-(Allyloxy)-2-methoxyphenethyl]-3-[5-chloro-2,3-dihydro-2-benzofuranylmethyl)imidazolium sulfate.

1-[2-(2-Butyloxy-2-(5-chloro-2-thienyl)ethyl]-3-[2,3-dihydro-2-benzofuranylmethyl)imidazolium acetate.

1-[2-(2-Butyloxy)-2-(2-thienyl)ethyl]-3-[5-bromo-2,3-dihydro-2-benzofuranylmethyl)imidazolium propionate.

1-[β-(3,4-Dimethylbenzyloxy)-2-isopropylphenethyl]-3-[5-chloro-2,3-dihydro-2-benzofuranylmethyl)imidazolium tartrate.

1-[β-(p-Cyanophenethyloxy)-4-(n-propoxy)phenethyl]-3-[2,3-dihydro-2-benzofuranylmethyl)imidazolium succinate.

1-[β-(2,4-Diaminophenoxy)-2-(2-thienyl)ethyl]-3-(5-fluoro-2,3-dihydro-2-benzofuranylmethyl)imidazolium citrate.

1-[β-(Benzyloxy)-2-methylphenethyl]-3-(p-chloro-β-hydroxyphenethyl)imidazolium iodide.

1-[β-(Allyloxy)-2-ethoxyphenethyl]-3-(p-methoxy-β-hydroxyphenethyl)imidazolium acetate.

1-[2-(2-Butynyloxy)-2-(5-chloro-2-thienyl)ethyl]-3-(p-bromo-β-hydroxyphenethyl)imidazolium nitrate.

1-[2-(2-Butyloxy)-2-(2-thienyl)ethyl]-3-(2,4-dichloro-β-hydroxyphenethyl)imidazolium succinate.

1-Cinnamyl-3-[β-(3,4-dimethylbenzyloxy)-2-isopropylphenethyl]imidazolium phosphate.

1-[β-(p-Cyanophenethyloxy)-4-(n-propoxy)phenethyl]-3-(p-fluorocinnamyl)imidazolium propionate.

1-[β-(2,4-Dinitrophenoxy)-2-(2-thienyl)ethyl]-3-(p-chlorocinnamyl)imidazolium methanesulfonate.

1-[β-(2,4-Diaminophenoxy)-2-(2-thienyl)ethyl]-3-[3-(p-chlorophenoxy)-2-oxopropyl]imidazolium tartrate.

1-[p-Cyanophenethyloxy-4-(n-propoxy)phenethyl]-3-(2,4-dibromophenoxy)-2-oxopropyl]imidazolium salicylate.

1-[β-(2,4-dimethylbenzyloxy)-2-isopropylphenethyl]-3-(2,4-dichlorophenoxy)-2-oxopropyl]imidazolium fumarate.

We claim:

1. A quaternary imidazolium salt represented by the structure

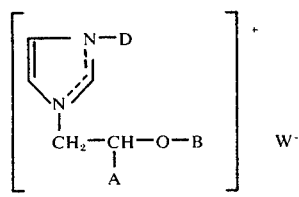

and hydrates thereof, wherein

A is a member selected from the group consisting of phenyl, mono- di- and trihalophenyl, lower alkyl phenyl, lower alkoxy phenyl, thienyl and halothienyl;

B is a member selected from the group consisting of benzyl, mono- di- and trihalobenzyl, mono- and di-lower alkylbenzyl, lower alkoxybenzyl, cyanobenzyl, phenethyl, mono-, di- and trihalophenethyl, mono- and di-lower alkylphenethyl, lower alkoxyphenethyl, cyanophenethyl, mono- and dinitrophenyl, mono- and di-aminophenyl, lower alkyl, lower alkenyl and lower alkynyl;

D is an aralkenyl radical represented by the formula

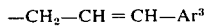

wherein $Ar^3$ is selected from the group consisting of phenyl, halophenyl and dihalophenyl; and W is a pharmaceutically acceptable anion selected from the group consisting of chloride, bromide, iodide, methanesulfonate, p-toluenesulfonate, nitrate, sulfate, phosphate, acetate, propionate, glycolate, lactate, pyruvate, malonate, succinate, maleate, fumarate, malate, tartrate, citrate, benzoate, cinnamate, mandelate, ethanesulfonate, benzenesulfonate, cyclohexanesulfamate, salicylate and p-aminosalicylate.

2. A composition for combating microorganisms comprising an inert carrier material and as an active ingredient an effective antimicrobial amount of quaternary imidazolium salt of claim 1.

3. A method of combating microorganisms which comprises contacting said microorganisms with an antimicrobial amount of a quaternary imidazolium salt of claim 1.

* * * * *

UNITED STATES PATENT AND TRADEMARK OFFICE
CERTIFICATE OF CORRECTION

PATENT NO. : 4,017,631
DATED : April 12, 1977
INVENTOR(S) : Paul Adriaan Jan Janssen; Jan Heeres; Hubert Karel Frans Hermans It is certified that error appears in the above-identified patent and that said Letters Patent are hereby corrected as shown below:

Column 1, Line 54, "alkyphe" should be -- alkylphe --.
Column 5, Line 40, "imidasolium" should be -- imidazolium --.
Column 5, Line 44, "silic" should be -- silica --.
Column 7, Line 13, "heloalkylcarbonamide" should be -- haloalkylcarbonamide --.
Column 10, Line 3, in the formula XVI, center, "$BrCH_2-CH-CH_2$" should be -- $BrCH_2-CH=CH_2$ --.
Column 27, Column D, 7 lines down, sub "CO" should be on the line and should read -- $-CH_2CO-NH-C_6H_3-2,4-(Cl)_2$ --.
Column 27, footnotes, "Sp.G=Salmonella pullerum" should be -- Sp. G=Salmonella pullorum --.
Column 27, footnotes, "E. coli = Excherichia" should be --E. Coli=Escherichia --.
Column 27, footnotes, insert -- *Growth observed at 100 µg/ml. --.
Column 30, Line 25, "Preparations" should be -- Preparation--
Column 33, Line 64, "silicugel" should be -- silica gel --.
Column 37, Line 47, "116.4°C." should be -- 116.5°C. --.
Column 37, Line 47, "116.5°C." as it now appears in heavy inking should be deleted.
Column 43, Line 63, "bromobenzoyl" should be -- Bromo-benzoyl --.
Column 44, Line 7, "dichlorophenethyl-]3" should be -- dichlorophenethyl]-3 --.
Column 44, Line 41, "chloroenzyloxy" should be -- chlorobenzyloxy --.
Column 44, Line 45, "chloroenzyloxy" should be -- chlorobenzyloxy) --.
Column 45, Line 57, "4-methyl2-" should be -- 4-methyl-2 --.

UNITED STATES PATENT AND TRADEMARK OFFICE
CERTIFICATE OF CORRECTION

PATENT NO. : 4,017,631

DATED : April 12, 1977

INVENTOR(S) : Paul Adriaan Jan Janssen; Jan Heeres; Hubert Karel Frans Hermans

It is certified that error appears in the above-identified patent and that said Letters Patent are hereby corrected as shown below:

Column 45, Line 63, "(o-tolyoxy)" should be -- (o-tolyloxy) --.
Column 46, "Example XLII" should be -- XLIII --.
Column 46, Line 8, "(2,4d-" should be -- (2,4- --.
Column 46, Line 41, "benzyl" should be -- benzyl] --.
Column 48, Line 25, "pfluorophenethyl" should be -- p-fluorophenethyl --.
Column 49, Line 18, "80 pars" should be -- 80 parts --.
Column 49, Line 23, "3-" should be -- 3-{ --.
Column 49, Line 23, between "ethyl" and "imidazolium" insert -- } --.
Column 49, Line 36, between "1-" and "1-[" insert -- { --.
Column 49, Line 36, between "ethyl" and "-3-[2,4-" insert -- } --.
Column 49, Line 39, between "1-" and "1-[" insert -- { --.
Column 49, Line 39, between "ethyl" and "-3-[2,4-" insert -- { --.
Column 49, Line 42, between "-3-" and "1-[N-(2,5-" insert -- { --.
Column 49, Line 45, between "1-" and "1-[" insert -- { --.
Column 49, Line 45, between "ethyl" and "-3-[2,4-" insert -- { --.
Column 50, Line 9, between "-3-" and "2-[N-(α,α,α,tri-" insert -- { --.
Column 50, Line 11, between "ethyl" and "imidazolium" insert -- { --.
Column 50, Line 33, between "-3-" and "2-[N-" insert -- { --.
Column 50, Line 39, between "-3-" and "2-[N-" insert -- { --.
Column 50, Line 42, between "1-" and "2-[N-" insert -- { --.
Column 50, Line 42, between "ethyl" and "-3-" insert -- { --.
Column 50, Line 48, between "1-" and "2-[N-" insert -- { --.
Column 50, Line 48, between "ethyl" and "-3-" insert -- } --.

UNITED STATES PATENT AND TRADEMARK OFFICE
CERTIFICATE OF CORRECTION

PATENT NO. : 4,017,631

DATED : April 12, 1977

INVENTOR(S) : Paul Adriaan Jan Janssen; Jan Heeres; Hubert Karel Frans Hermans

It is certified that error appears in the above-identified patent and that said Letters Patent are hereby corrected as shown below:

```
Column 53, Line 61, "zyl-oxy" should be -- zyloxy --.
Column 54, Line 61, "-2,4di" should be -- -2,4-di --.
Column 54, Line 67, "-3-1" should be -- -3-{ 1 --.
Column 55, Line 4,  "(2,4dichloro" should be
                    -- (2,4-dichloro --.
Column 55, Line 12, "ethyl-3" should be -- ethyl{-3 --.
Column 55, Line 28, "-3-1" should be -- -3-{ 1 --.
Column 55, Line 29, between "ethyl" and "imidazolium"
                    insert -- } --.
Column 55, Line 56, between "ethyl" and "imidazolium"
                    insert -- } --.
Column 56, Lines 23-24, "phenethyl]-3-2" should be
                    -- phenthyl]-3-{ 2 --.
Column 56, Line 24, after "ethyl" insert -- } --.
Column 57, Line 29, "equiivalent" should be -- equivalent --.
Column 59, Line 42, at the beginning of the line insert
                    -- { --.
Column 59, Line 42, between "ethyl" and "imidazolium"
                    insert -- { --.
Column 59, Line 47, "ethy ]-3-" should be -- ethyl]-3-{ --.
Column 59, Line 47, and Line 48, after "ethyl" insert
                    -- } --.
Column 59, Line 67, "ethyl-3" should be -- ethyl]-3 --.
```

Signed and Sealed this

Twenty-first Day of November 1978

[SEAL]

Attest:

RUTH C. MASON
Attesting Officer

DONALD W. BANNER
Commissioner of Patents and Trademarks